United States Patent [19]

Bilofsky et al.

[11] 3,932,455

[45] Jan. 13, 1976

[54] CARBAZOLE PHTHALEINS

[75] Inventors: Ruth C. Bilofsky, Arlington, Mass.; Richard D. Cramer, Wallingford, Pa.

[73] Assignee: Polaroid Corporation, Cambridge, Mass.

[22] Filed: May 22, 1974

[21] Appl. No.: 472,162

Related U.S. Application Data

[63] Continuation-in-part of Ser. No. 202,482, Nov. 26, 1971, Pat. No. 3,816,119.

[52] U.S. Cl. .............................................. 260/315

[51] Int. Cl.² ...................................... C07D 209/86

[58] Field of Search .................................... 260/315

[56] References Cited

UNITED STATES PATENTS

| | | | |
|---|---|---|---|
| 3,491,111 | 1/1970 | Lin | 260/315 |
| 3,647,437 | 3/1972 | Land | 96/84 R |
| 3,702,244 | 11/1972 | Bloom et al. | 96/3 |

*Primary Examiner*—Sherman D. Winters
*Attorney, Agent, or Firm*—Sybil A. Campbell

[57] ABSTRACT

This invention relates to a new class of indicator dyes useful as optical filter agents in photographic processes to protect a selectively exposed photosensitive material from further exposure during processing in the presence of incident light. Such dyes comprise 3,6-disubstituted carbazoles wherein the 3,6 substituents are selected from a phthalidyl radical, $$\overline{C_6H_4.CO.O.C}R—,$$

wherein R is an aryl group and an o-carboxybenzoyl radical, not more than one of said substituents being o-carboxybenzoyl.

52 Claims, 1 Drawing Figure

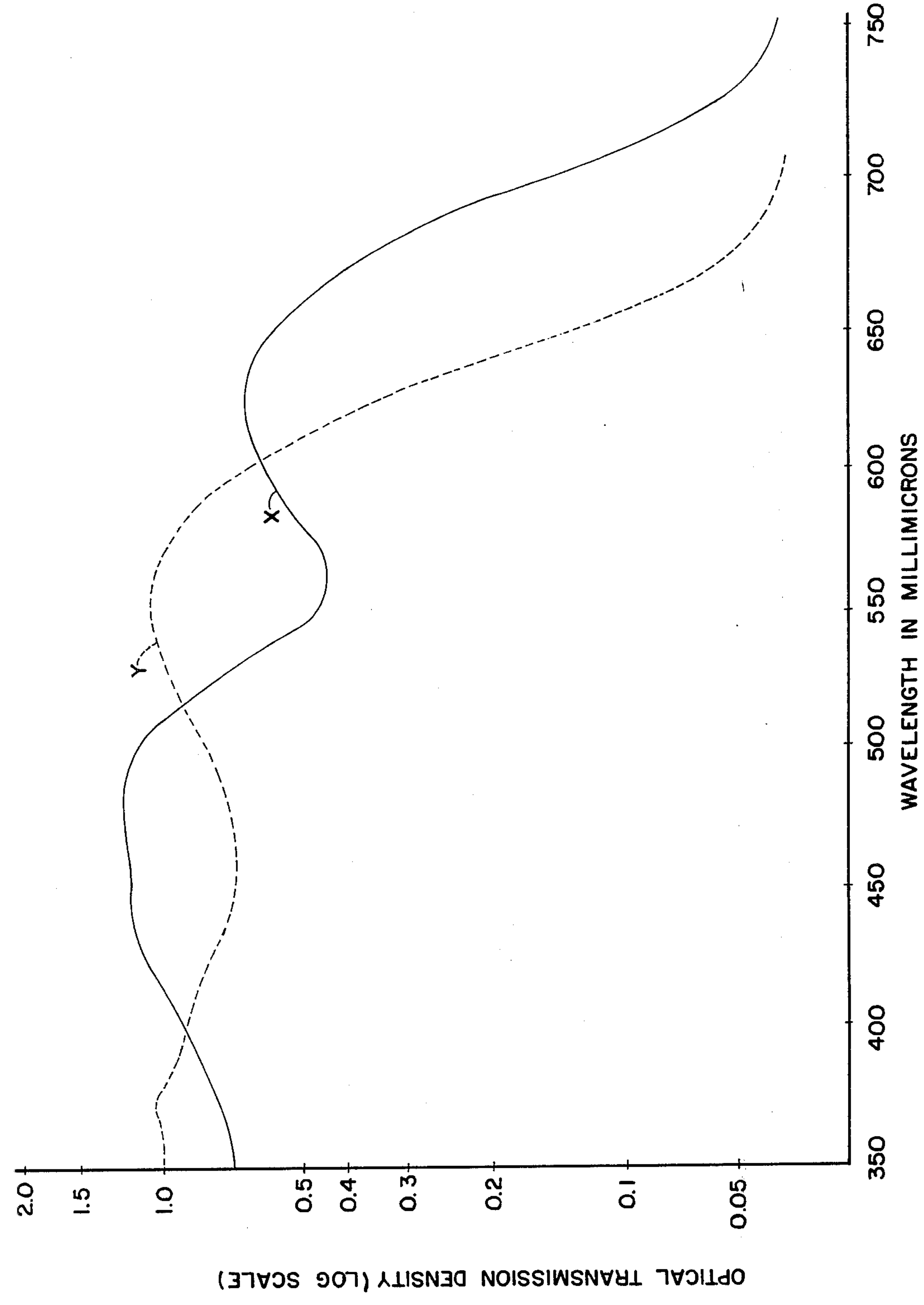
OPTICAL TRANSMISSION DENSITY (LOG SCALE)
2.0
1.5
1.0
0.5
0.4
0.3
0.2
0.1
0.05
WAVELENGTH IN MILLIMICRONS
350
400
450
500
550
600
650
700
750
X
Y

CARBAZOLE PHTHALEINS

CROSS-REFERENCE TO RELATED PATENT APPLICATIONS

This application is a continuation-in-part of my copending application Ser. No. 202,482 filed Nov. 26, 1971, now U.S. Pat. No. 3,816,119.

BACKGROUND OF THE INVENTION

1. Field of the Invention

The present invention relates to novel chemical compounds, and more specifically, it relates to a new class of pH sensitive indicator dyes. In a particular aspect, it relates to indicator dyes derived from certain 3,6-disubstituted carbazoles useful as optical filter agents in photographic processes for protecting an exposed photosenstive material from post-exposure fogging during development in the presence of extraneous incident light and to such photographic uses.

2. Description of the Prior Art

A number of photographic processes by which images may be developed and viewed within seconds or minutes after exposure have been proposed. Such processes generally employ a processing composition which is suitably distributed between two sheet-like elements, the desired image being carried by one of said sheet-like elements. The resulting images may be in black-and-white, e.g., in silver, or in one or more colors. Processing may be conducted in or outside of a camera. The most useful of such processes are the diffusion transfer processes which have been proposed for forming silver or dye images, and several of these processes have been commercialized. Such processes have in common the feature that the final image is a function of the formation of an image-wise distribution of an image-providing reagent and the diffusion transfer of said distribution to or from the stratum carrying the final image, whether positive or negative.

U.S. Pat. No. 3,415,644 discloses a composite photosensitive structure, particularly adapted for use in reflection type photographic diffusion transfer color processes. This structure comprises a plurality of essential layers including, in sequence, a dimensionally stable opaque layer; one or more silver halide emulsion layers having associated therewith dye image-providing material which is soluble and diffusible, in alkali, at a first pH, as a function of the point-to-point degree of its associated silver halide emulsion's exposure to incident actinic radiation; a polymeric layer adapted to receive solubilized dye image-providing material diffusing thereto; a polymeric layer containing sufficient acidifying capacity to effect reduction of a processing composition from the first pH to a second pH at which the dye image-providing material is substantially nondiffusible; and a dimensionally stable transparent layer. This structure may be exposed to incident actinic radiation and processed by interposing, intermediate the silver halide emulsion layer and the reception layer, an alkaline processing composition providing the first pH and containing a light-reflecting agent, for example, titanium dioxide to provide a white background. The light reflecting agent (referred to in said patent as an "opacifying agent") also performs an opacifying function, i.e., it is effective to mask the developed silver halide emulsions and also acts to protect the photoexposed emulsions from post-exposure fogging by light passing through the transparent layer if the photoexposed film unit is removed from the camera before image formation is complete.

In a preferred embodiment, the composite photosensitive structure includes a rupturable container, retaining the alkaline processing composition having the first pH and light-reflecting agent, fixedly positioned extending transverse a leading edge of the composite structure in order to effect, upon application of compressive pressure to the container, discharge of the processing composition intermediate the opposed surfaces of the reception layer and the next adjacent silver halide emulsion.

The liquid processing composition distributed intermediate the reception layer and the silver halide emulsion, permeates the silver halide emulsion layers of the composite photosensitive structure to initiate development of the latent images contained therein resultant from photoexposure. As a consequence of the development of the latent images, dye image-providing material associated with each of the respective silver halide emulsion layers is individually immobilized as a function of the point-to-point degree of the respective silver halide emulsion layer photoexposure, resulting in imagewise distributions of mobile dye image-providing materials adapted to transfer, by diffusion, to the reception layer to provide the desired transfer dye image. Subsequent to substantial dye image formation in the reception layer, a sufficient portion of the ions of the alkaline processing composition transfers, by diffusion, to the polymeric neutralizing layer to effect reduction in the alkalinity of the composite film unit to the second pH at which dye image-providing material is substantially nondiffusible, and further dye image-providing material transfer is thereby substantially obviated.

The transfer dye image is viewed, as a reflection image, through the dimensionally stable transparent layer against the background provided by the reflecting agent, distributed as a component of the processing composition, intermediate the reception layer and next adjacent silver halide emulsion layer. The thus-formed stratum effectively masks residual dye image-providing material retained in association with the developed silver halide emulsion layer subsequent to processing.

In the copending U.S. patent application Ser. No. 786,352 of Edwin H. Land, filed Dec. 23, 1968, now abandoned, and application Ser. No. 101,968 filed Dec. 28, 1970, now U.S. Pat. No. 3,647,437, in part a continuation of application Ser. No. 786,352, an organic light absorbing reagent (or optical filter agent), such as a dye, which is present as a light-absorbing species at the first pH and which may be converted to a substantially non-light-absorbing species at the second pH is used in conjunction with the light-reflecting agent to protect the selectively exposed silver halide emulsions from post-exposure fogging when development of the photo-exposed emulsions is conducted in the presence of extraneous incident actinic radiation impinging on the transparent layer of the film unit.

In copending U.S. Pat. application Ser. No. 108,260 filed Jan. 21, 1971, now U.S. Pat. No. 3,702,244, pH-sensitive dyes which contain at least one indole radical bonded by the 2- or 3-position to a ring-closing moiety are disclosed as useful as optical filter agents for absorbing incident radiation actinic to selectively exposed photosensitive materials within a predetermined wavelength range in the shorter wavelength region of the visible spectrum. Certain of the novel indicator dyes disclosed therein, namely, those derived from certain 3,6-di-substituted carbazoles are among the dyes comprising the subject matter of the present invention.

SUMMARY OF THE INVENTION

It is the primary object of the present invention to provide a novel class of indicator dyes derived from certain carbazoles.

It is another object of the present invention to provide a novel class of indicator dyes useful as optical filter agents in photographic processes for preventing post-exposure fogging of a selectively exposed photosensitive material during development in the presence of incident light.

It is a further object of the present invention to provide products, compositions and processes for the development of photosensitive materials in which the novel indicator dyes are used.

It is yet a further object of the present invention to provide a novel process for the preparation of these indicator dyes.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

According to the present invention, there is provided a novel class of indicator dyes comprising 3,6-disubstituted carbazoles wherein said 3,6 substituents are selected from a phthalidyl radical, $C_6H_4.CO.O.CR$—, wherein R is an aryl group and an o-carboxybenzoyl radical, not more than one of said substitutents being o-carboxybenzoyl. These indicator dyes will be defined with greater particularity hereinafter.

Like pH sensitive dyes in general, the dyes of the present invention exhibit reversibly alterable spectral absorption characteristics in response to changes in environmental pH. They have a colored, light-absorbing form in alkaline media at a first pH value above their pKa and a substantially colorless form, i.e., a form which is substantially non-light-absorbing in the visible spectrum at a second pH below their pKa. By pKa is meant the pH at which about 50% of the dye is present in its light-absorbing form and about 50% is present in its non-light-absorbing form.

It will be appreciated that such compounds will find utility in titrations and other analytical procedures where pH sensitive indicator dyes are commonly employed, for example, to measure changes in pH value as reflected by the change in color of the dye from one color to another or from colored to colorless or vice versa. The indicator dyes of the present invention, however, due particularly to their spectral absorption characteristics are especially useful as optical filter agents in photographic processes where development of a selectively exposed photosensitive material is performed at least in part outside the confines of a camera in the presence of extraneous incident actinic radiation.

For a fuller understanding of the nature and objects of the invention, reference should be had to the following detailed description taken in connection with the accompanying drawing.

Brief Description of the Drawing

The FIGURE is a graphic illustration of the spectral absorption characteristics of two indicator dyes of the present invention and represents the optical transmission density, i.e., absorbance of the respective dyes measured on a logarithm scale over the wavelength range of 350 nm. to 750 nm. in aqueous alkaline solution at a pH substantially above their pKa.

DESCRIPTION OF THE PREFERRED EMBODIMENTS

According to the present invention, it has been found that the above-denoted 3,6-disubstituted carbazole indicator dyes exhibit remarkably broad spectral absorption characteristics in the visible spectrum and that dyes may be selected from this class that absorb radiation substantially throughout the visible range. Moreover, the dyes of the present invention are efficient absorbers of radiation within the broad range which renders them particularly useful as optical filter agents for photographic processes.

Typical of the indicator dyes of the present invention are those represented by the following formula:

(I)

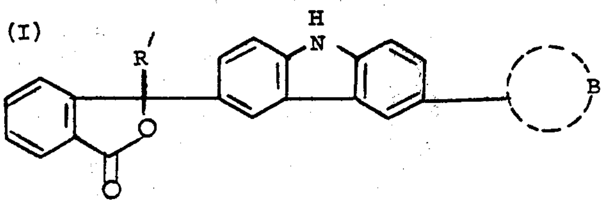

wherein B represents

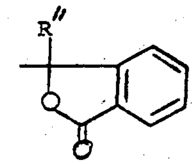

or

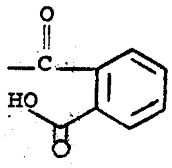

and R' and R'' are aryl groups. When both carbazole substituents are phthalidyl radicals, such dyes will be referred to herein as "carbazeins". In a like manner, when one substituent is a phthalidyl radical and the other is a carboxybenzoyl radical, the dyes will be referred to as "hemicarbazeins." The carbazeins and hemicarbazeins embraced by the above formula are illustrated in formulae I*a* and I*b*, respectively.

(Ia)

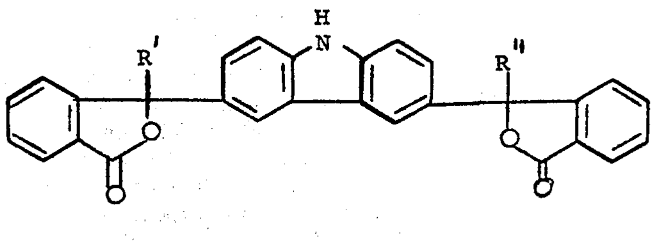

(Ib) 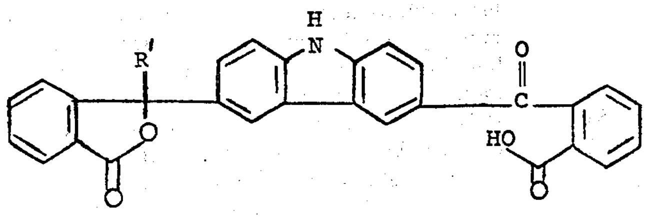

In the above formulae, R' and R'' have the same meaning as given in formula (I) above. The R' and R'' substituents may be any aromatic radical, substituted or unsubstituted, e.g., carbocyclic aryl of the benzene or naphthanlene series or heterocyclic aryl containing O, N, S, P and combinations thereof. Illustrative of suitable R' and R'' groups are those derived from N-heterocyclic compounds, such as, pyrrole, indole, carbazole, pyridine, quinoline, pyridazine; S-heterocyclic compounds, such as, thiophene, thiazole, benzothiophene; O-heterocyclic compounds, such as, furan, benzofuran, oxazole; P-heterocyclic compounds, such as, phosphazole, phosphene; and carbocyclic compounds, such as, benzene, naphthalene, and especially carbocyclic aryl with para substituents, such as, hydroxyl and amino including mono- and di- N-substituted amino. Preferred groups include, pyrr-2-yl, indol-3-yl, carbazol-3-yl, p-hydroxyphenyl, p-hydroxynaphthyl and p-N-substituted aminophenyl. Because of the convenience in preparation, the R' and R'' groups in the carbazein dyes, as illustrated in formula (I*a*), preferably are identical.

The indicator dyes defined above and as represented in the foregoing formulae may contain substituents other than those specified as may be desired which do not interfere with the function of the dye for its selected ultimate use. Where it is desired that the indicator dye be substantially immobile or non-diffusible in the processing solution, it may be substituted with a bulky group, such as, a long chain substituent, e.g., dodecyloxy, hexadecyl or dodecylphenyl. Also, it may be substituted with solubilizing groups, e.g., carboxy or sulfo to adjust the solubility in a given solution and with appropriate groups, such as, hydrogen-bonding groups to adjust the pKa for use in a given photographic process.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as; phenyl, 2-hydroxyphenyl, and naphthyl; alkaryl, such as benzyl, phenethyl, phenylhexyl, p-octylphenyl, p-dodecylphenyl; alkoxy, such as, methoxy, ethoxy, butoxy, 1-ethoxy-2-(β-ethoxyethoxy), dodecyloxy and octadecyloxy; aryloxy, such as phenoxy, benzyloxy, naphthoxy; alkoxyalkyl, such as methoxyethyl, dodecyloxyethyl; halo such as, fluoro, bromo, and chloro; trifluoralkyl, such as, trifluoromethyl, mono- and bis-trifluoromethyl carbinol; sulfonamido; sulfamoyl; acyl and its derivatives; aminomethyl; amido; sulfonyl; sulfo; cyano; nitro; amino including mono-and disubstituted amino, e.g., N-ethyl amino and N,N'-dimethylamino; carboxy; and hydroxyl.

As noted above, it may be desirable to adjust the pKa of the subject dyes for use in a given photographic process, e.g., by substituting a hydrogen-bonding group capable of raising the pKa on a carbon atom adjacent to the —NH— of an N-heterocyclic aryl radical or on a carbon atom adjacent to the —OH of a p-hydroxycarbocyclic aryl radical comprising R' and R''. The association of two atoms through hydrogen to form a hydrogen bond between or within molecules is well known. When hydrogen is attached to an electronegative atom, for example, O or N, the resultant bond is polarized. If directed toward another atom (M) with an unshared pair of electrons, the hydrogen acts as a bridge between the atoms (O-H . . . M) due to the electrostatic attraction to both atoms between which the hydrogen proton can be transferred. In the present invention an intramolecular hydrogen bond is formed between the p-hydroxy group of a p-hydroxy carbocyclic aryl radical, e.g., p-hydroxyphenyl or p-hydroxynaphthyl, or the —NH— of an N-heterocyclic aryl radical, e.g., indol-3-yl or pyrr-2-yl and an adjacent hydrogen-bonding group, i.e., a group containing a heteroatom possessing an active unshared pair of electrons, such as, O, N, S or halogen, e.g., F, which has a free electron pair of negative charge in basic solution and which is capable of forming a 5-, 6-, or 7-membered and preferably a 5- or 6-membered hydrogen-bonded ring with the p-hydroxy group of the carbocyclic aryl radical or the —NH— of the N-heterocyclic aryl radical. Preferably, the heteroatom in the hydrogen-bonding group has attached to it a proton which is more acidic than the proton on the -NH- or functional —OH and ionizes in basic solution to a negative charge. Such groups include, for example, carboxy; hydroxy; o-hydroxyphenyl; bis trifluoromethyl carbinol; sulfonamido (-NH-$SO_2$-R) and sulfamoyl ($SO_2$-NH-R°) wherein R and R° are hydrocarbon groups containing up to 20 carbon atoms and may be alkyl, aryl, aralkyl, particularly phenyl-substituted alkyl and alkaryl, particularly alkyl-substituted phenyl. Suitable R and R° substituents include branched or straight chain alkyl, e.g., methyl, ethyl, isopropyl, n-butyl, t-butyl, hexyl, octyl, dodecyl, hexadecyl, octadecyl and eicosanyl; aryl, e.g., phenyl and naphthyl; aralkyl and alkaryl, e.g., benzyl, phenethyl, phenylhexyl, p-octylphenyl and p-dodecylphenyl.

In a preferred embodiment, the indicator dyes of the present invention are compounds of formula I

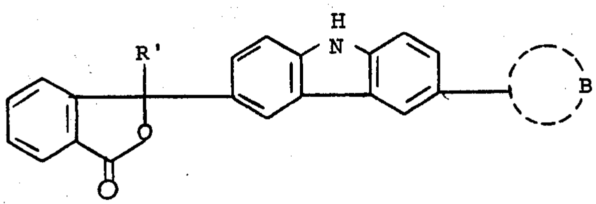

wherein B represents

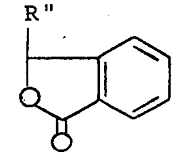

or

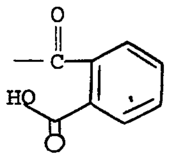

wherein R′ and R″ the same are selected from

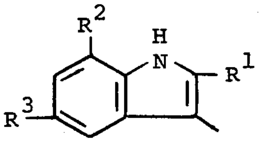

,

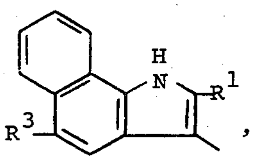

,

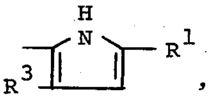

,

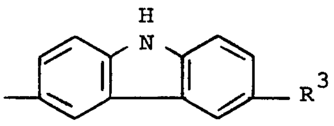

,

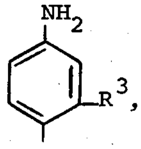

,

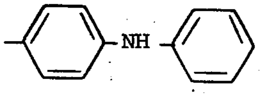

,

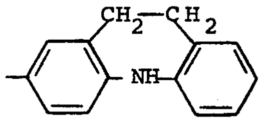

,

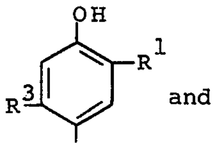

and

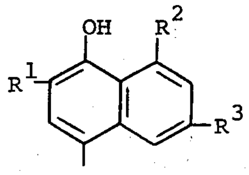

wherein $R^1$ is selected from hydrogen, alkyl having 1 to 20 carbon atoms, phenyl and a hydrogen-bonding group forming a 5-, 6- or 7-membered intramolecular hydrogen-bonded ring with the adjacent -NH- or -OH and selected from carboxy, hydroxy, o-hydroxyphenyl, bis trifluoromethyl carbinol, sulfonamido and sulfamoyl, $R^2$ is selected from hydrogen and a hydrogen-bonding group forming a 5-, 6- or 7-membered intramolecular hydrogen-bonded ring with the adjacent -NH- or -OH and selected from carboxy, hydroxy, o-hydroxyphenyl, bis trifluoromethyl carbinol, sulfonamido and sulfamoyl, not more than one of $R^1$ and $R^2$ being a hydrogen-bonding group, and $R^3$ is selected from hydrogen, phenyl, alkyl having 1 to 20 carbon atoms, and alkoxy having 1 to 20 carbon atoms. In a particularly preferred embodiment, R′ and R″ of the carbazeins and hemicarbazeins are derived from indoles.

Specific examples of indicator dyes within the scope of the present invention are as follows:

(1)

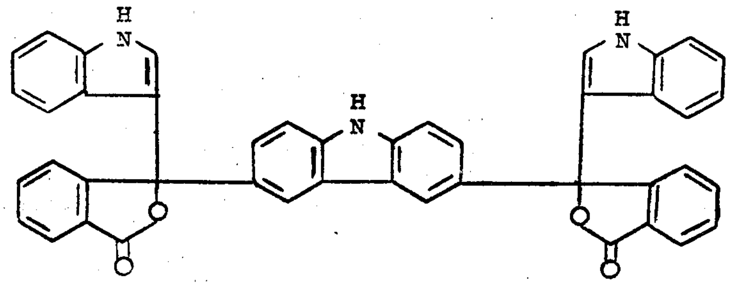

(2)

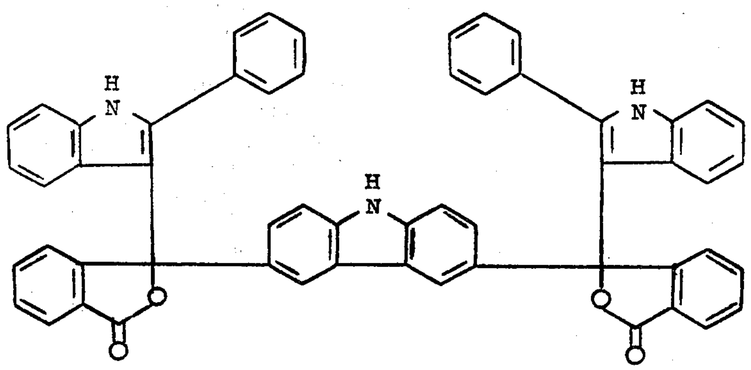

(3)
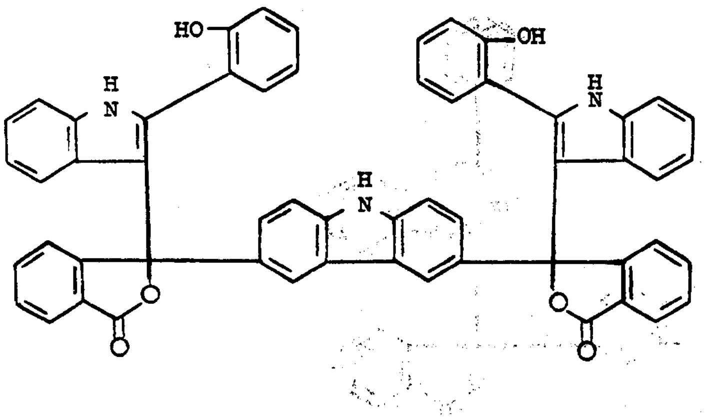
(4)
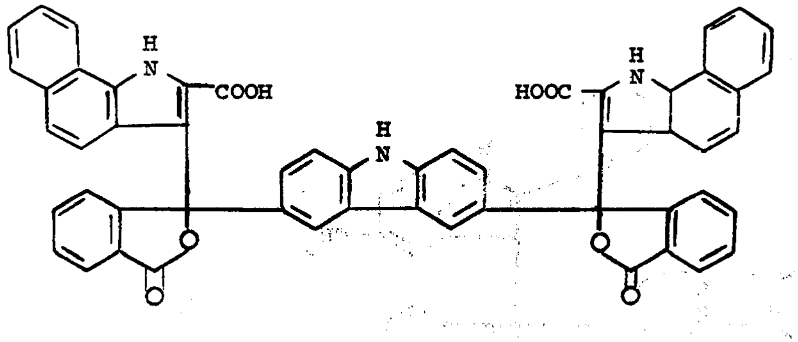
(5)
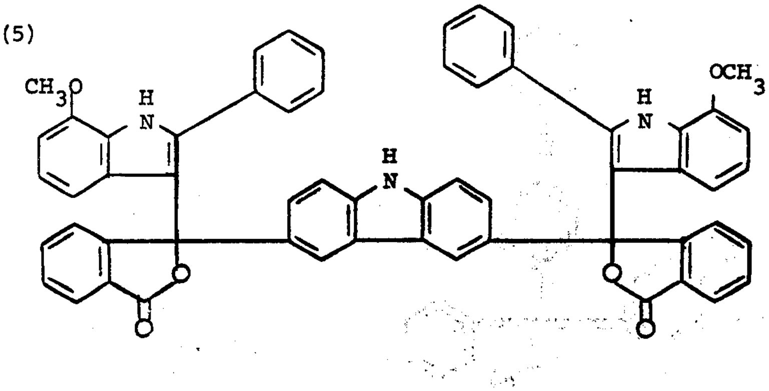
(6)
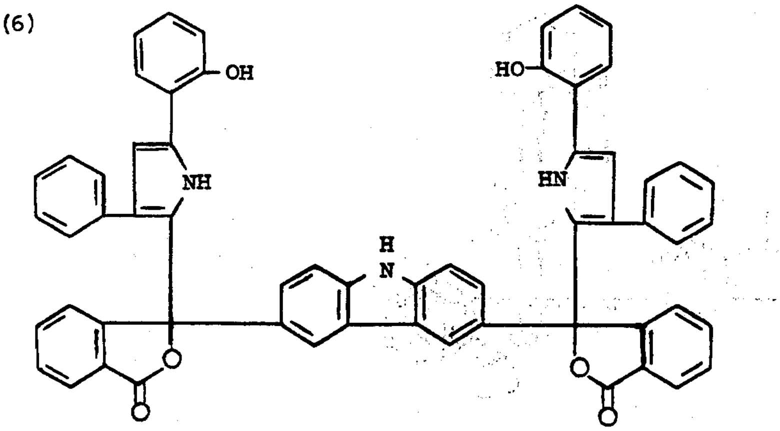

(7)
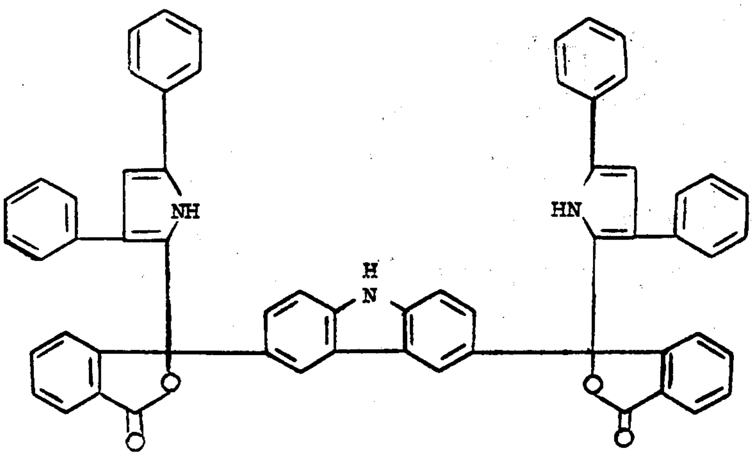
(8)
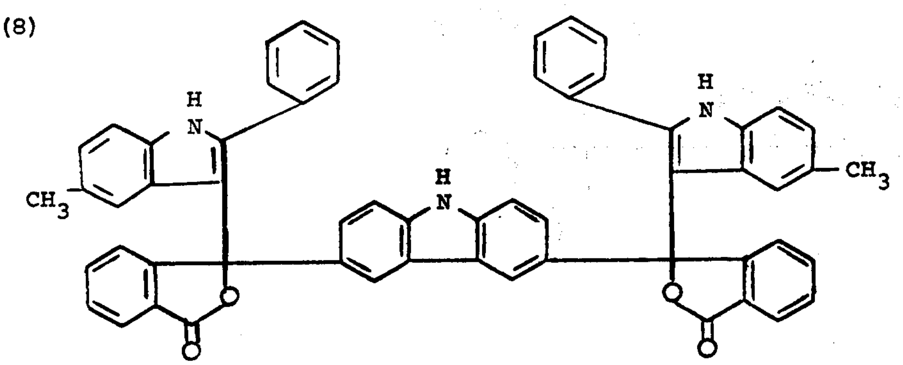
(9)
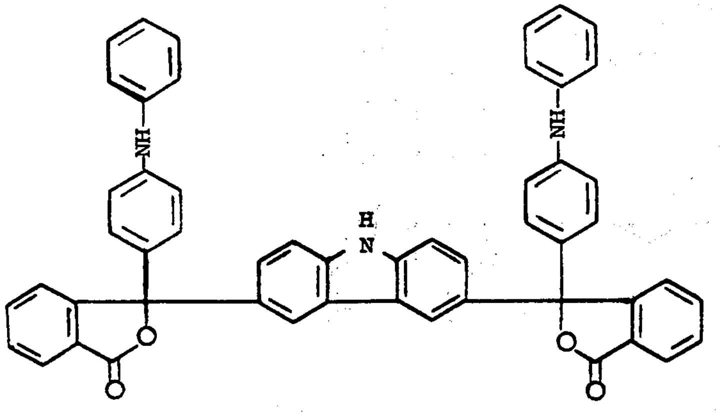
(10)
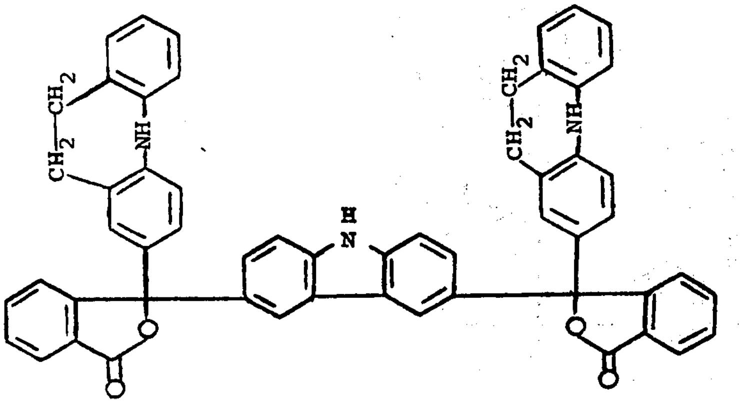

(11)
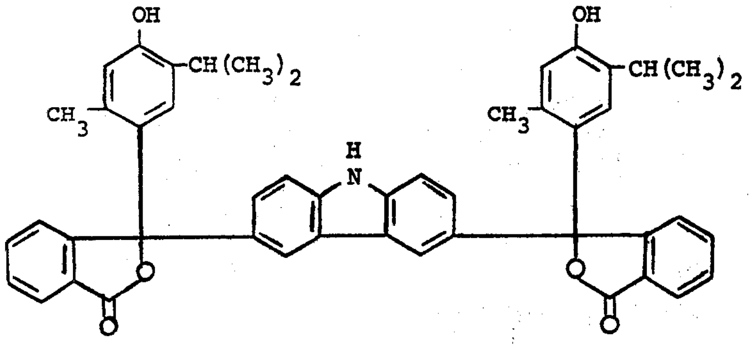
(12)
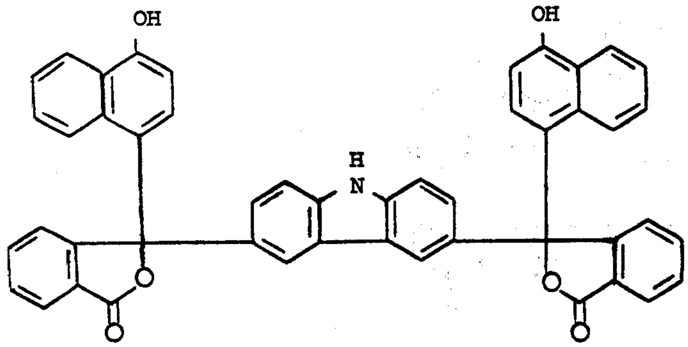
(13)
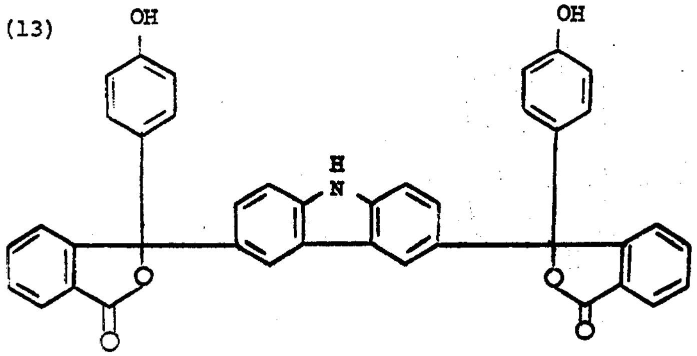
(14)
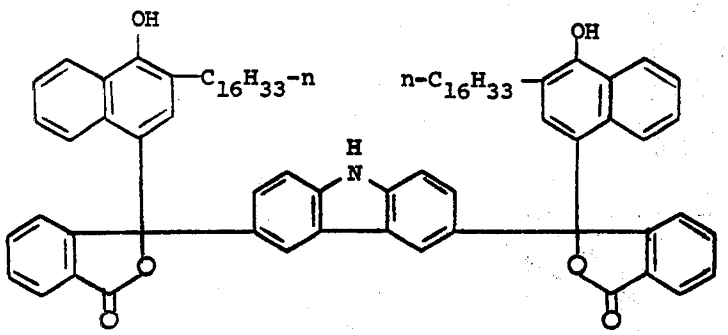

(15)
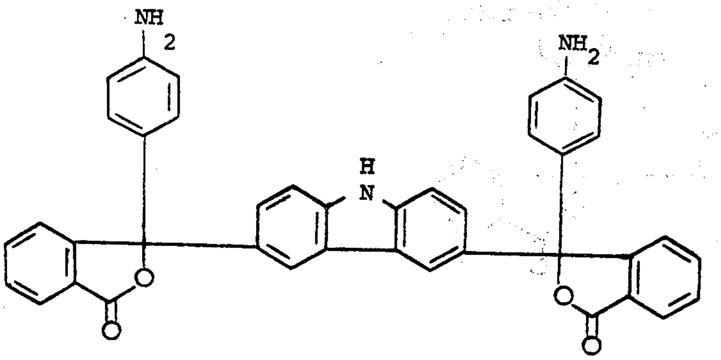
(16)
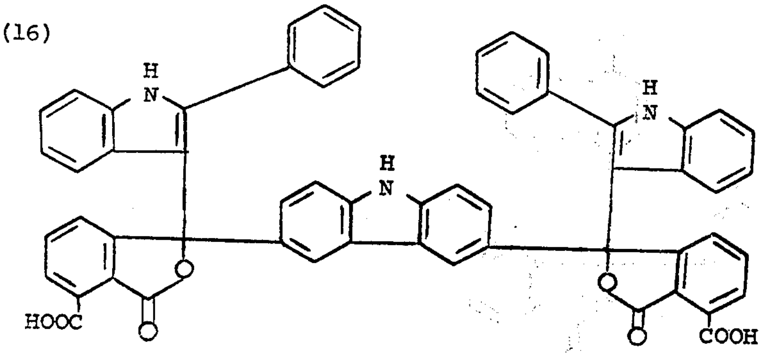
(17)
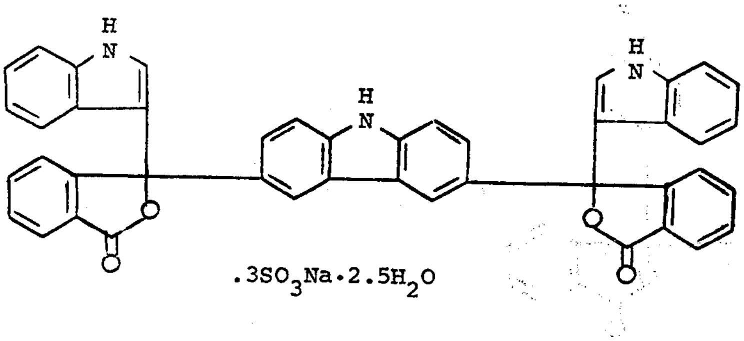
$.3SO_3Na \cdot 2.5H_2O$
(18)
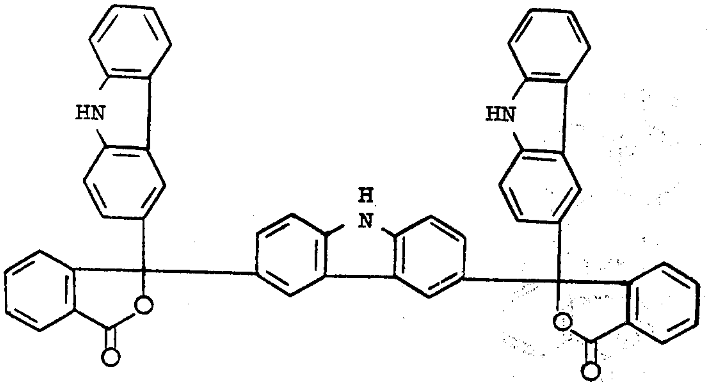

(19)
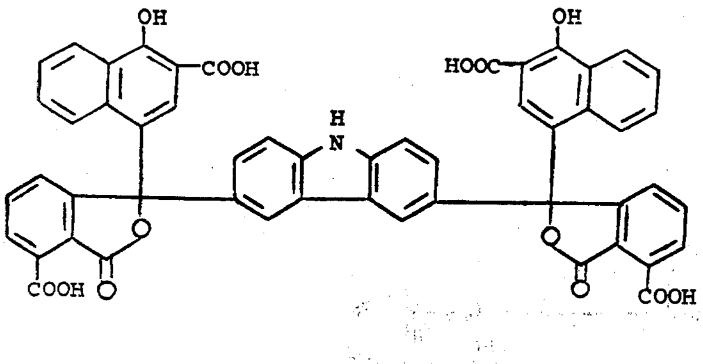
(20)
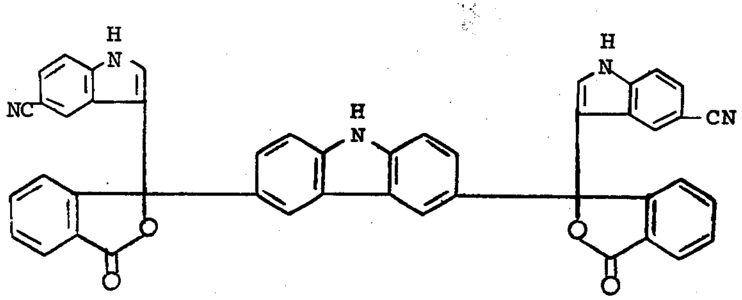
(21)
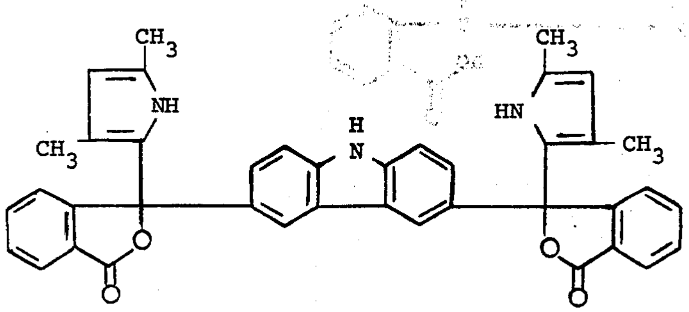
(22)
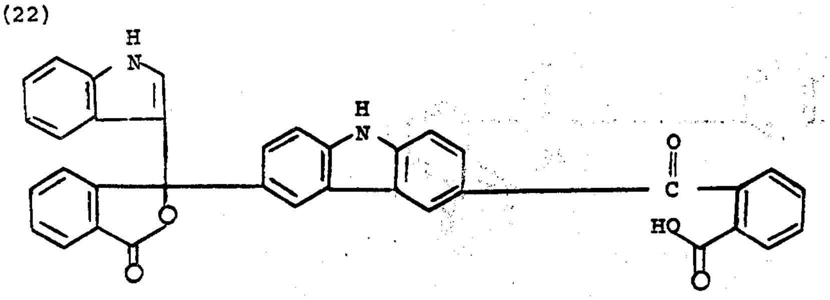
(23)
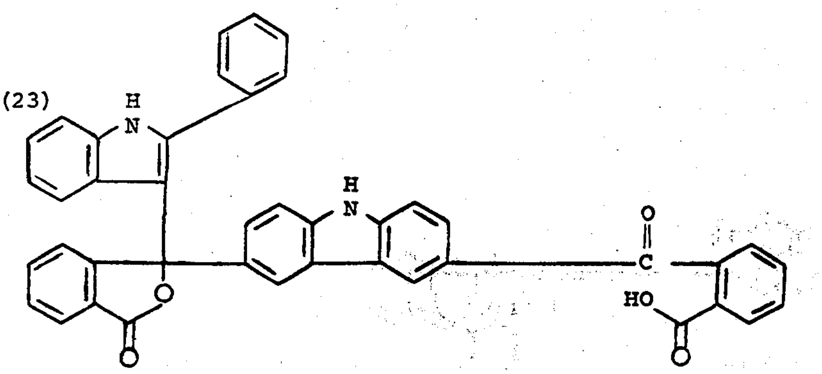

(24)
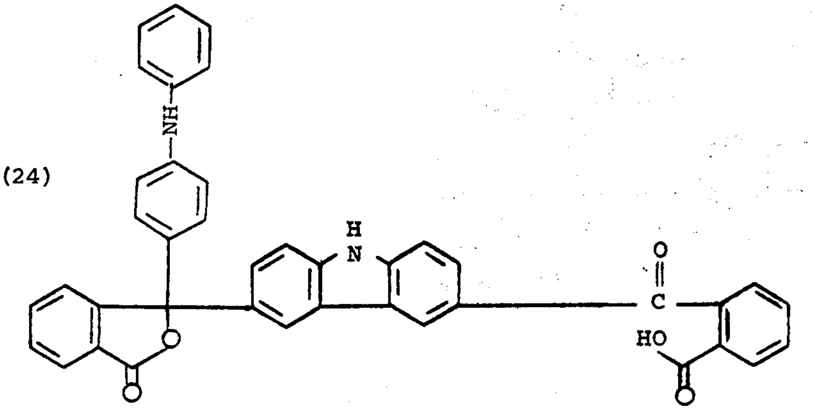
(25)
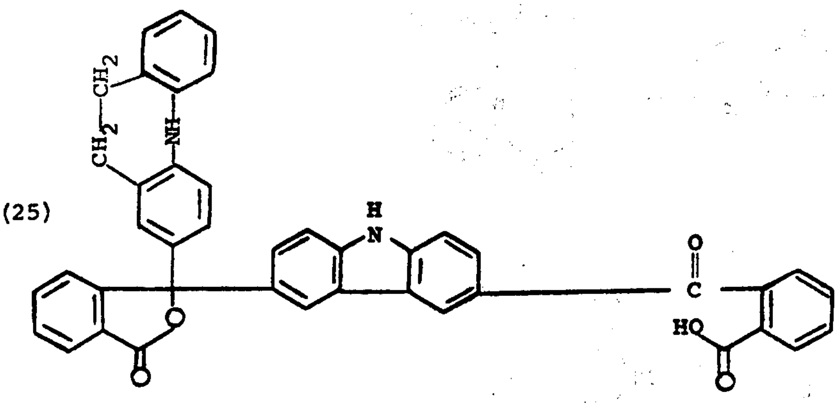
(26)
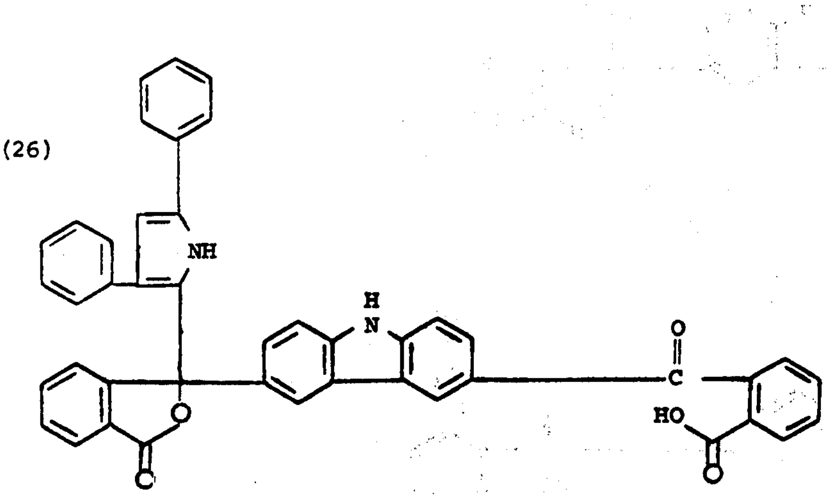
(27)
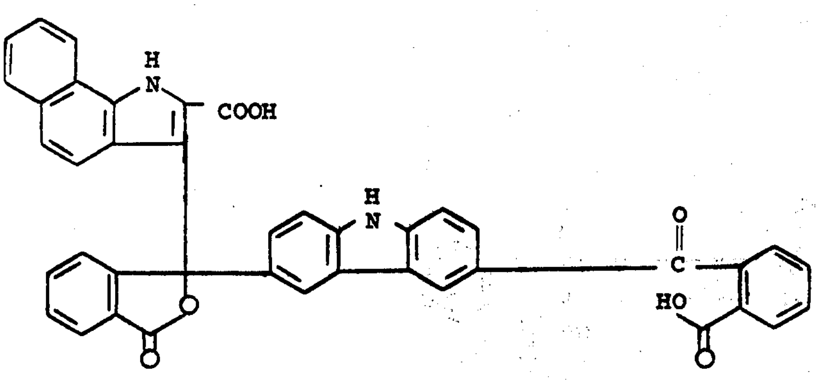

(28)
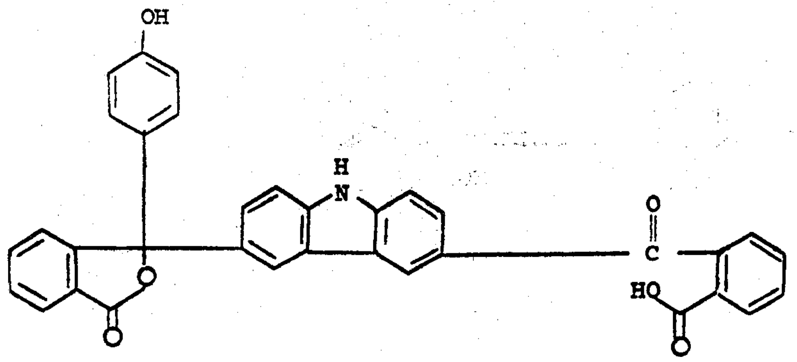
(29)
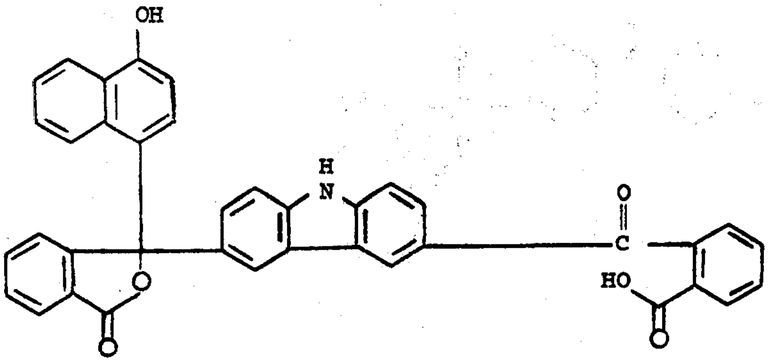
(30)
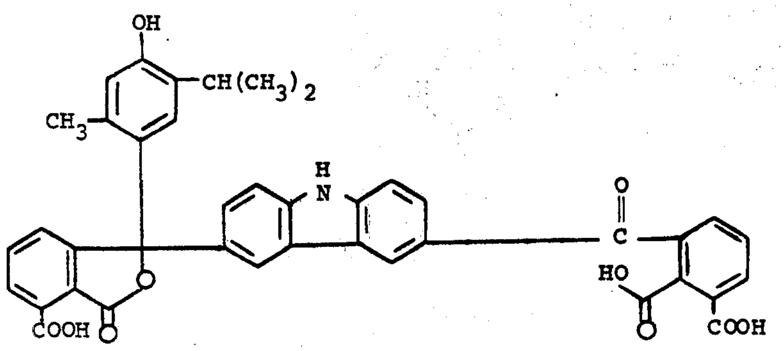
(31)
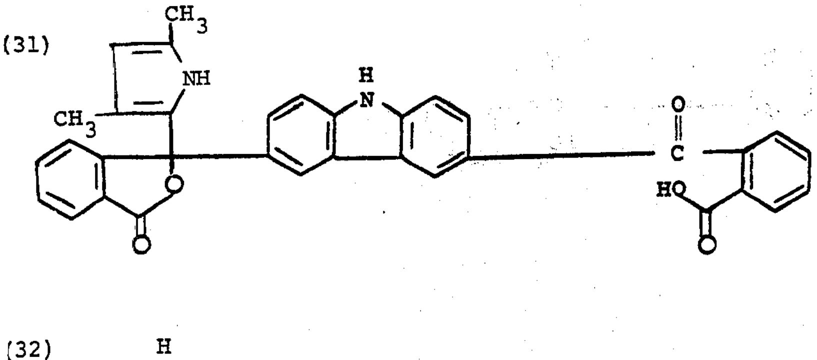
(32)
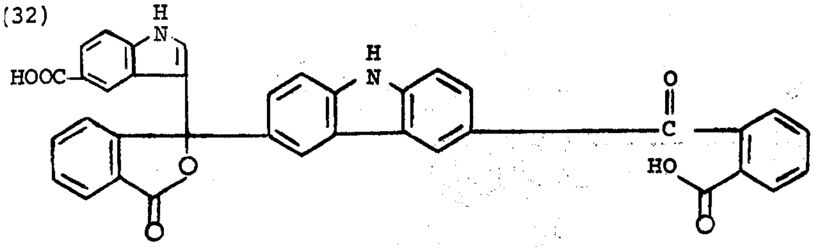

(33)
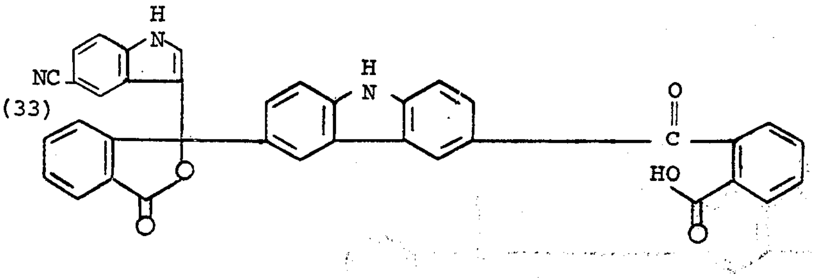
(34)
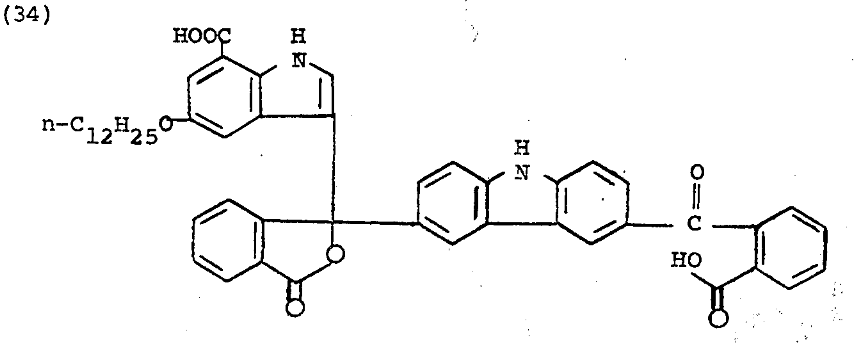
(35)
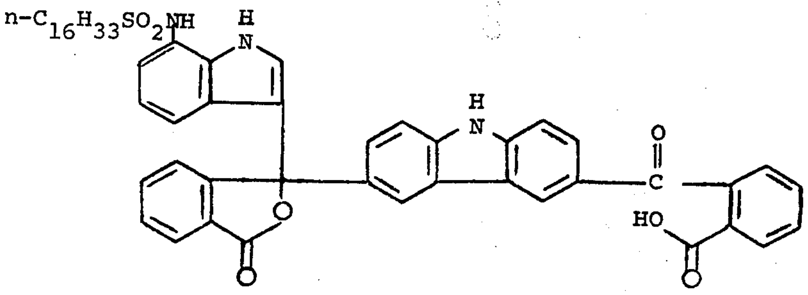
(36)
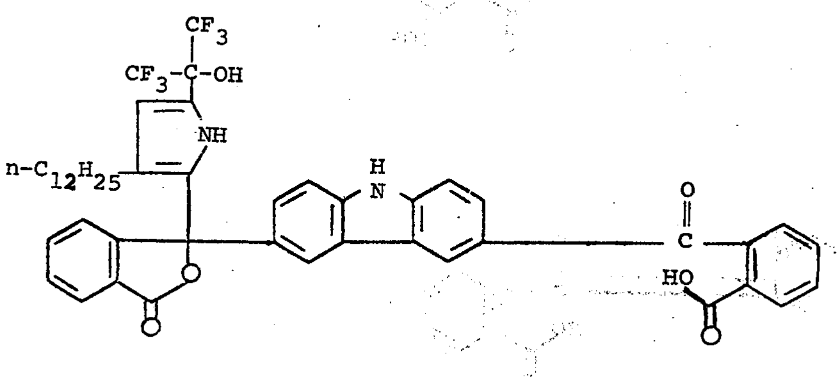
(37)
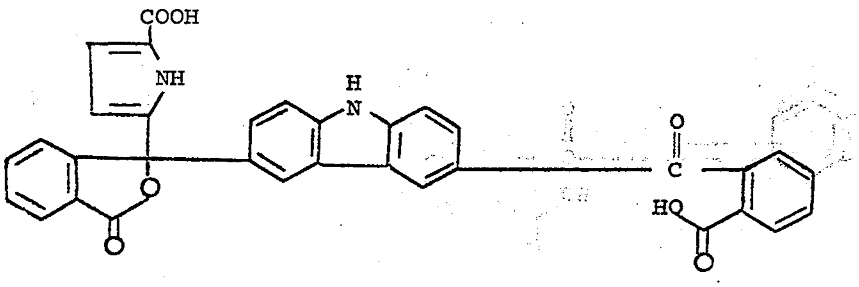

(38)
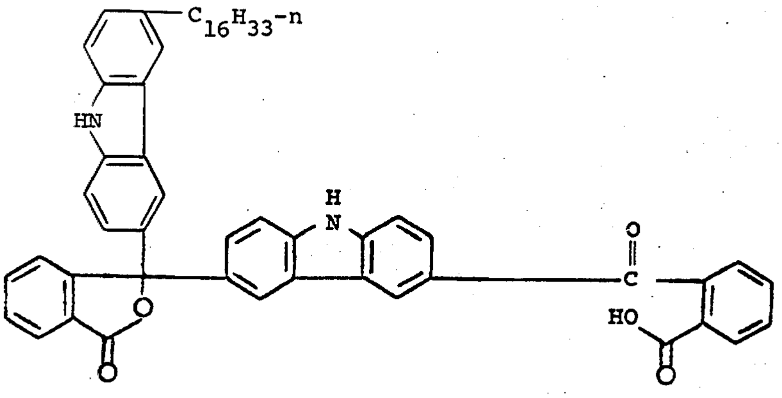
(39)
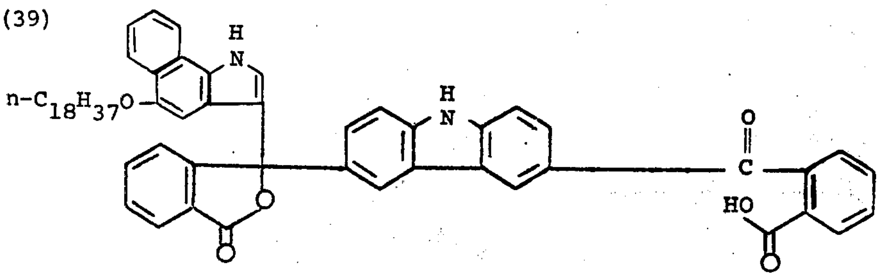
(40)
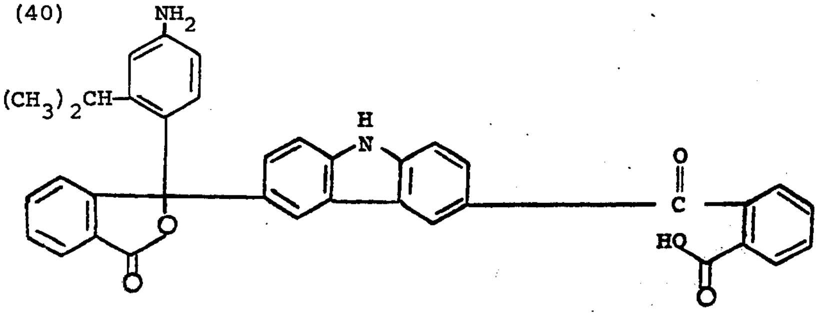
(41)
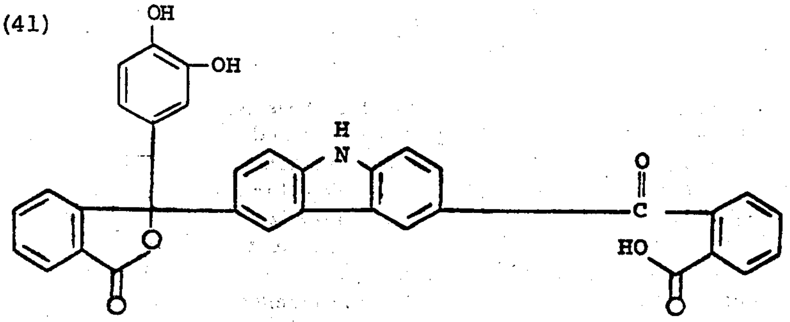
(42)
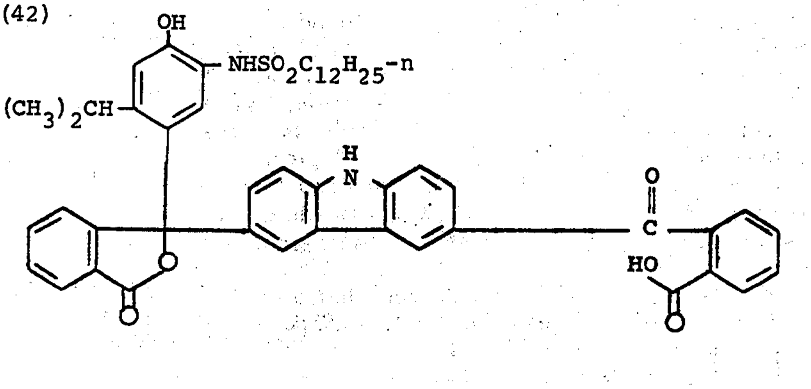

(43)
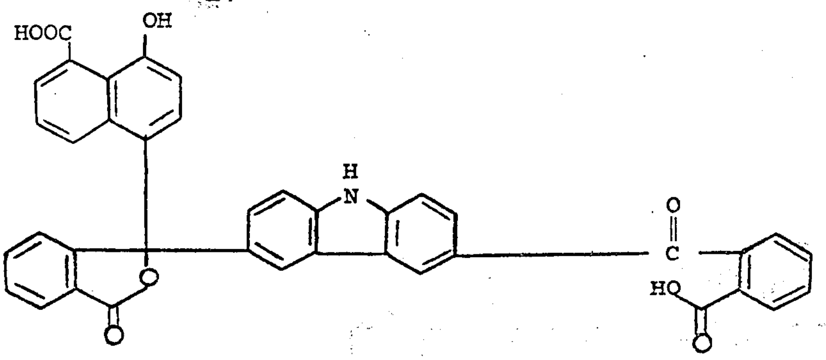

(44)
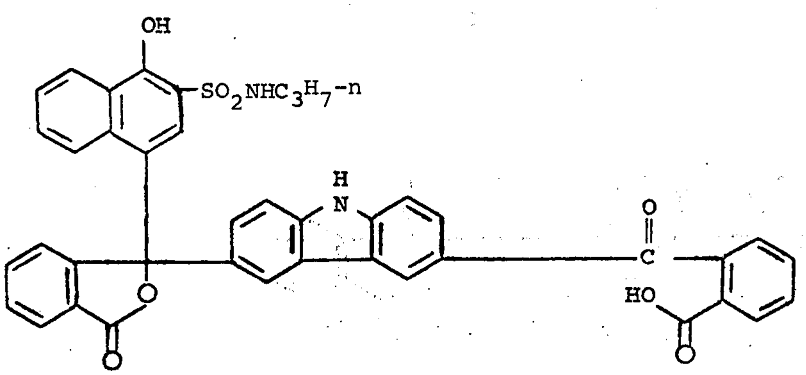

(45)
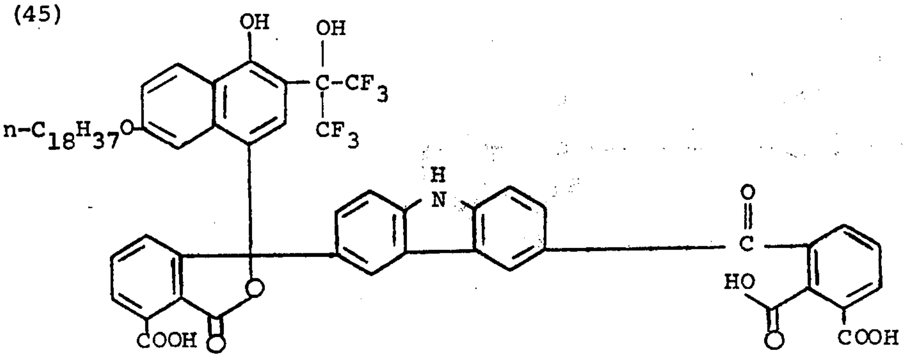

The indicator dyes of the present invention are conveniently prepared by reacting a 3,6-bis-(orthocarboxybenzoyl)carbazole and the aromatic compound selected to provide the R' and R'' radicals in the presence of a suitable condensing agent. Depending upon the aromatic compound, the condensing agent may be acetic anhydride, an acid catalyst, such as, a Lewis acid, e.g., p-toluenesulfonic acid, zinc chloride and boron trifluoride or other condensing agent as conventionally employed in reactions of this type. It has been found that acetic anhydride is useful as the condensing agent with heterocyclic compounds, such as, indoles and pyrroles, and that boron trifluoride-etherate is particularly useful with carbocyclic aryl compounds, such as, phenols and anilines.

The aromatic compound may be any of those enumerated previously and may be unsubstituted or may contain substituents such as those mentioned previously. Likewise, the orthocarboxybenzoyl carbazole starting material may contain substituents, for example, sulfonic acid groups, sulfonic acid salt groups, carboxy groups or other groups as may be desired in the final dye product.

In the synthesis of carbazeins, two equivalents of aromatic compound are reacted with one equivalent of the carbazole starting material. If desired, the aromatic compound may be employed in a slight excess. Hemicarbazeins may be synthesized by reacting one or slightly less than one equivalent of the aromatic compound with one equivalent of carbazole. The synthesis of hemicarbazeins in this manner, however, is not altogether satisfactory. The desired product usually is formed in only small amounts and is difficult to isolate from the reaction mixture.

It has now been found quite unexpectedly that hemicarbazeins may be obtained in greatly improved yields and purity by forming the carbazein first and then treating the carbazein with strong alkali to yield the corresponding hemicarbazein. In preparing these compounds according to this procedure, ≧ 2 equivalents of aromatic compound and 1 equivalent of a 3,6-bis-(ortho-carboxybenzoyl)carbazole are reacted in the presence of a condensing agent to form the carbazein which is treated with strong alkali, usually an aqueous or aqueous-alkanol solution of an alkaline hydroxide preferably at elevated temperature to yield the corresponding carbazein. The alkaline hydroxide may be any alkali metal or alkaline earth metal hydroxide. For example, hemicarbazeins may be formed at a practical reaction rate and in good yields by heating in an aqueous alkanol solution of sodium hydroxide.

The carbazeins of the present invention are most conveniently prepared by refluxing ≧ 2 equivalents of the selected N-heterocyclic compound, e.g., indole, pyrrole or carbazole and 1 equivalent of 3,6-bis-(ortho-carboxybenzoyl) carbazole in acetic anhydride or by refluxing ≧ 2 equivalents of the selected carbocyclic compound, e.g., phenol, 1-naphthol, aniline or diphenylamine and 1 equivalent of 3,6-bis-(orthocarboxybenzoyl)carbazole in boron-trifluoride etherate. The hemicarbazeins are preferably synthesized from the corresponding carbazein by refluxing the carbazein in an aqueous methanol or aqueous ethanol solution of 5–10% by weight sodium hydroxide.

The following examples are given to further illustrate the present invention and are not intended to limit the scope thereof.

EXAMPLE 1

Preparation of indole carbazein, formula (1):

Indole (0.505 g., 0.00432 mole), 3,6-bis-(orthocarboxybenzoyl)carbazole (1.0 g., 0.00216 mole) and acetic anhydride (50 mls.) were heated together for three hours at reflux. Excess anhydride was decomposed with a mixture of acetic acid-water. Additional water was added, and the solid that formed was filtered and then recrystallized from ethanolacetic acid to give the title compound.

EXAMPLE 2

Preparation of 2-phenylindole carbazein, formula (2):

The title compound was prepared according to the procedure of Example 1 above using 0.00432 mole of 2-phenylindole, 0.00216 mole of 3,6-bis-(ortho-carboxybenzoyl)carbazole and 100 mls. of acetic anhydride.

EXAMPLE 3

Preparation of 2-phenylindole hemicarbazein, formula (23).

A mixture of 2-phenylindole (0.00432 mole), 3,6-bis-(ortho-carboxybenzoyl)carbazole (0.00216 mole), and acetic anhydride (100 mls.) was refluxed for 3 hours. The excess anhydride was decomposed with water-acetic acid, and additional water was added until precipitation was complete. The precipitate was collected and added to an aqueous methanol solution of 5% sodium hydroxide. The solution was refluxed overnight. Hydrochloric acid was added to the solution and the precipitate obtained was put on a basic alumina column with acetone. After elution with 200 mls. of methanol, the column was eluted with ammonium hydroxide. The ammonium hydroxide solution collected was acidified and the solid formed was filtered and recrystallized from acetone-water. The acetonewater recrystallization was repeated to give the title compound, substantially pure, in a yield of about 10% by weight.

As a comparison, the procedure of Example 2 was repeated using half the amount of carbazole. A mixture of products was obtained including both the carbazein and hemicarbazein of 2-phenylindole. The amount of hemicarbazein in the crude reaction mixture was about 1% by weight.

The 3,6-bis-(ortho-carboxybenzoyl)carbazole used in the above examples was prepared according to the procedure reported by Scholl and Neovins, Ber., vol. 44, p. 1249 (1911) by reacting carbazole and phthalic anhydride in organic solution in the presence of aluminum chloride.

The carbazeins represented in formulas 3 to 8 and 18 were prepared following the procedure of Example 1 above by reacting the appropriate aromatic compound with the 3,6-bis carbazole. The carbazeins of formulae 9 to 12 also were prepared according to the procedure of Example 1 except that the condensing agent employed in the reaction of the aromatic compound and carbazole was boron trifluoride-etherate. The hemicarbazeins of formulae 24 and 25 were prepared following the procedure of Example 3.

It will be appreciated that other indoles, pyrroles, phenols and 1-naphthols such as those substituted with hydrogen-bonding groups or other indoles, pyrroles, phenols, 1-naphthols, carbazoles and anilines such as those substituted with alkyl or alkoxy groups to adjust mobility of the dye in a given solution may be employed in the procedure of Example 1 with the appropriate condensing agent to yield the corresponding carbazein. The carbazein dye product in turn may be refluxed in an aqueous methanol solution of sodium hydroxide according to the procedure of Example 3 to yield the corresponding hemicarbazein.

The spectral absorption characteristics of the 2-phenylindole carbazein and 2-phenylindole hemicarbazein produced above are graphically illustrated in the accompanying FIGURE and are designated therein as (X) and (Y), respectively. The curves for (X) and (Y) represent the optical transmission density, i.e., the absorbance of the respective dyes at a pH substantially above their respective pKa as measured in aqueous sodium hydroxide solution.

From reference to the FIGURE, it will be apparent that the 2-phenylindole carbazein and hemicarbazein are good absorbers of radiation over a very extensive wavelength range in the visible spectrum. The unusually broad spectral absorption as illustrated in the FIGURE is characteristic of carbazeins and hemicarbazeins in general including the phenol, naphthol, diphenylaniline and other such dyes produced above. Though simple mixed carbazole phthaleins also are good absorbers of radiation in the visible spectrum, the corresponding carbazeins and hemicarbazeins absorb over a much broader wavelength range. By simple mixed carbazole phthaleins is meant 3,3-disubstituted phthalides where one of the 3 substituents is a carbazol-3-yl radical without the pthalidyl or carboxybenzoyl radical and the other 3 substituent is a radical derived from a different aromatic compound. Mixed carbazole/indole phthaleins of this type form the subject matter of copending U.S. patent application Ser. No. 202,555 of Paul S. Huyffer filed Nov. 26, 1971.

The pKa values measured for 2-phenylindole carbazein (formula 2) were 11.6 and 14.6 and for the corresponding hemicarbazein (formula 23) were 10.5 and 13.8. The first and second pKa measured for 2-(o-hydroxyphenyl)indole carbazein (formula 3) were 14.0 and 16.5, respectively. The thymol and 1-naphthol carbazeins of formulae 11 and 12 possessed a first pKa in the vicinity of 13 to 14.

For use as optical filter agents in photographic processes, such as, diffusion transfer processes employing alkaline processing solutions having a pH of 12 or higher, it may be desirable that the indicator dye selected as the optical filter agent possess a relatively high pKa so that the dye will be in a light-absorbing form during the initial stages of processing and yet may be rendered substantially non-light absorbing within a relatively brief interval as the pH is reduced to permit early viewing of the final image. Preferably, the indicator dye selected will have a first pKa of about 11 or higher. In photographic processes employing less alkaline processing compositions, it may be desirable to select an indicator dye having a lower pKa, and thus, dyes of the above-denoted class will be selected accordingly.

The pH sensitive indicator dyes of the present invention may be used as optical filter agents in any photographic process including conventional tray processing and diffusion transfer photographic techniques. In such processes, the dye or dyes during development of a selectively exposed photosensitive material will be in a position and in a concentration effective to absorb a given level of non-selective radiation incident on and actinic to the photosensitive material. The dyes may be initially disposed in the film unit, for example, in a layer(s) coextensive with one or both surfaces of the photosensitive layer. Where selective exposure of the photosensitive material is made through a layer containing the indicator dye, then the dyes should be in a non-light-absorbing form until the processing solution is applied. Alternately, the dyes may be initially disposed in the processing composition in their light-absorbing form, for example, in the developing bath in tray processing or in the layer of processing solution distributed between the photosensitive element and the superposed image-receiving element (or spreader sheet) in diffusion transfer processing. The particular indicator dye or dyes selected should have an absorption spectrum corresponding to the sensitivity of the photosensitive layer, so as to afford protection over the predetermined wavelength range required by the particular photosensitive material employed and should have a pKa such that they are in their colored form, i.e., light-absorbing form at the pH at which the photographic process is performed. Most commercially useful photographic processes are performed under alkaline conditions. Diffusion transfer processes, for example, usually employ highly alkaline processing solutions having a pH in excess of 12.

In photographic processes where the optical filter agent is retained in a stratum through which the final image is to be viewed, the color of the indicator dye may be discharged subsequent to image formation by adjusting the pH of the system to a value at which the dye is substantially non-light absorbing in the visible spectrum. In photographic processes performed at an alkaline pH, the optical filter agent, such as, a dye or dyes of the present invention are rendered substantially colorless by reducing the environmental pH. In processes where the optical filter agent is removed or separated from the layer containing the final image or retained in a layer that does not interfere with viewing of the final image, it is unnecessary to convert the indicator dye to its non-light-absorbing form, though the color may be discharged if desired.

The concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. It has been found, by interposing neutral density (carbon containing) filters over a layer of titanium dioxide, that a transmission density of approximately 6.0 from said neutral density filters was effective to prevent fogging of a diffusion transfer multicolor film unit of the type described in said U.S. Pat. No. 3,415,644 having a transparent support layer and an Equivalent ASA Exposure Index of approximately 75, when processed for one minute in 10,000 foot candles of color corrected light, a light intensity approximating the intensity of a noon summer sun. The transmission density required to protect such a film unit under the stated conditions may also be expressed in terms of the "system" transmission density of all the layers intermediate the silver halide layer(s) and the incident light; the "system" transmission density required to protect color film units of the aforementioned type and photographic speed has been found to be on the order of 7.0 to 7.2. Lesser levels of optical transmission density would, of course, provide effective protection for shorter processing times, lesser light intensities and/or films having lower exposure indices. The transmission density and the indicator dye concentration necessary to provide the requisite protection from incident light may be readily determined for any photographic process by following the above described procedure or obvious modifications thereof.

Since most commercial photographic processes employ photosensitive materials sensitive to and exposable by actinic radiation throughout the visible spectrum, e.g., black-and-white panchromatic silver halide emulsions and multilayer silver halide emulsion elements, it is preferred to use a mixture of two or more of the subject dyes or a second dye(s) in conjunction with the subject dye(s) that has a principal absorption in a second and at least partially different predetermined wavelength range such that the combination of dyes will afford protection from non-selective incident actinic radiation over the range of 400 to 700 nm. If a second dye is employed with the subject dyes, it may be non-color-changing but preferably, is also pH sensitive, i.e., has reversibly alterable spectral absorption characteristics in response to changes in the environmental pH so that it may be rendered light-absorbing or non-light-absorbing as desired, for example, an appropriate phthalein. The second dye also may be initially present in the film unit or in the processing composition as discussed above either together with or separate from the subject dyes and subsequent to processing may be removed from the film unit or retained within the film structure, provided it is in a form or position such that it does not interfere with viewing of the image produced.

Dyes may be selected from those described above that are particularly useful as optical filter agents in diffusion transfer processes, for example, those employing composite diffusion transfer photosensitive elements including a film pack or roll wherein superposed photosensitive and image-receiving elements are maintained as a laminate after formation of the final image. Such elements include at least one transparent support to allow viewing of the final image without destroying the structural integrity of the film unit. Preferably, the support carrying the photosensitive layer(s) is opaque and the support carrying the image-receiving layer is transparent and selective photoexposure of the photosensitive layer(s) and viewing of the final image both are effected through the latter support. The final image is viewed as a reflection print, i.e., by reflected light, provided by a reflecting agent initially disposed in the processing composition applied and maintained intermediate the image-receiving and next adjacent photosensitive layer or by a preformed layer of reflecting agent initially positioned intermediate the image-receiving and next adjacent photosensitive layer. It will be understood that a preformed reflecting layer, while it should be capable of masking the photosensitive layer(s) subsequent to image formation, should not interfere with selective photoexposure of the photosensitive material prior to processing.

When utilizing reflection-type composite film units, the indicator dye or dyes employed as the optical filter agent(s) may be positioned initially in a layer of the film unit, e.g., in a layer between the image-receiving and next adjacent photosensitive layer through which photo-exposure is effected provided it is incorporated under conditions, i.e., at a pH such that it will not absorb actinic radiation intended to selectively expose the photosensitive material to form a latent image therein. For example, the optical filter agent may be in a layer coated over either the image-receiving layer or the next adjacent photosensitive layer and should remain substantially non-light-absorbing until a processing composition is applied providing a pH at which the indicator dye is capable of being rapidly converted to its light-absorbing form to provide light protection when the film unit is removed from the camera. Rather than being initially disposed in the film unit, the indicator dye may be initially present in the processing composition applied intermediate the image-receiving and next adjacent photosensitive layer subsequent to photoexposure. The dye, when initially disposed in the processing composition, will be in its light-absorbing form.

The dyes selected as optical filter agents should exhibit at the initial pH of the processing, maximum spectral absorption of radiation at the wavelengths to which the film unit's photosensitive silver halide layer or layers are sensitive, and preferably, should be substantially immobile or non-diffusible in the alkaline processing composition in order to achieve optimum efficiency as a radiation filter and to prevent diffusion of filter agent into layers of the film unit where its presence may be undesirable. Recognizing that the filter agent absorption will detract from image-viewing characteristics by contaminating reflecting pigment background, the selected agents should be those exhibiting major spectral absorption at the pH at which processing is effected and minimal absorption at a pH below that which obtains during transfer image formation. Accordingly, the selected optical filter agent or agents should possess a pKa below that of the processing pH and above that of the environmental pH subsequent to transfer image formation.

As discussed previously, the concentration of indicator dye is selected to provide the optical transmission density required, in combination with other layers intermediate the silver halide emulsion layer(s) and the incident radiation, to prevent nonimagewise exposure, i.e., fogging, by incident actinic light during the performance of the particular photographic process. In the processes where the indicator dye or dyes selected as optical filter agents are used in conjunction with a reflecting agent or agents, the optical filter agents and reflecting agents together should possess the optical transmission density necessary to protect the photosensitive material for the particular photographic process. The optimum concentration of optical filter agent(s) or filter agent(s) together with reflecting agent(s) may be readily determined empirically for each photographic system.

While substantially any reflecting agent may be employed for the layer of reflecting agent, either preformed or applied as a component of the processing composition, it is preferred to select an agent that will not interfere with the color integrity of the dye transfer image, as viewed by the observer, and, most preferably, an agent which is aesthetically pleasing to the viewer and does not provide a background detracting from the information content of the image. Particularly desirable reflecting agents will be those providing a white background, for viewing the transfer image, and specifically those conventionally employed to provide background for reflection photographic prints and, especially, those agents possessing the optical properties desired for reflection of incident radiation.

As examples of reflecting agents, mention may be made of barium sulfate, zinc sulfide, titanium dioxide, barium stearate, silver flake, silicates, alumina, zirconium oxide, zirconium acetyl acetate, sodium zirconium sulfate, kaolin, mica, and the like.

Illustrative of the photographic use of the indicator dyes of the present invention as optical filter agents, a photographic film unit may be prepared by coating, in succession, on a gelatin subbed, 4 mil. opaque polyethylene terephthalate film base, the following layers:

1. a layer of the cyan dye developer 1,4-bis-(β-[hydroquinonyl-α-methyl]-ethylamino)-5,8-dihydroxy-anthraquinone dispersed in gelatin and coated at a coverage of about 80 $mgs./ft.^2$ of dye and about 100 $mgs./ft.^2$ of gelatin;
2. a red-sensitive gelatino-silver iodobromide emulsion coated at a coverage of about 225 $mgs./ft.^2$ of silver and about 50 $mgs./ft.^2$ of gelatin;
3. a layer of the acrylic latex sold by Rohm and Haas Co., Philadelphia, Pennsylvania, U.S.A., under the trade designation AC-61 and polyacrylamide coated at a coverage of about 150 $mgs./ft.^2$ of AC-61 and about 5 $mgs/ft.^2$ of polyacrylamide;
4. a layer of the magenta dye developer 2-(p-[6 β-hydroquinonylethyl]-phenylazo)-4-isopropoxy-1-naphthol dispersed in gelatin and coated at a coverage of 70 $mgs./ft.^2$ of dye and about 120 $mgs./ft.^2$ of gelatin;
5. a green-sensitive gelatino-silver iodobromide emulsion coated at a coverage of about 120 $mgs./ft.^2$ of silver and 60 $mgs./ft.^2$ of gelatin;
6. a layer comprising the acrylic latex sold by Rohm and Haas Co. under the trade designation B-15 and polyacrylamide coated at a coverage of about 100 $mgs./ft.^2$ of B-15 and about 10 $mgs./ft.^2$ of polyacrylamide;
7. a layer of the yellow dye developer 4-(p-[β-hydroquinonylethyl]-phenylazo)-3-(N-n-hexyl-carboxamide)-1-phenyl-5-pyrazolone and the auxiliary developer 4'-methylphenyl hydroquinone dispersed in gelatin and coated at a coverage of about 50 mgs./$ft.^2$ of dye, about 15 mgs./$ft.^2$ of auxiliary developer and 50 mgs./$ft.^2$ of gelatin;

8. a blue-sensitive gelatino-silver iodobromide emulsion coated at a coverage of about 75 mgs./$ft.^2$ of silver and about 75 mgs./$ft.^2$ of gelatin; and
9. a layer of gelatin coated at a coverage of about 50 mgs./$ft.^2$ of gelatin.

Then a transparent 4 mil. polyethylene terephthalate film base may be coated, in succession, with the following illustrative layers:

1. a 7:3 mixture, by weight, of polyethylene/maleic acid copolymer and polyvinyl alcohol at a coverage of about 1400 mgs./$ft.^2$, to provide a polymeric acid layer;
2. a graft copolymer of acrylamide and diacetone acrylamide on a polyvinyl alcohol backbone in a molar ratio of 1:3.2:1 at a coverage of about 800 mgs./$ft.^2$, to provide a polymeric spacer layer; and
3. a 2:1 mixture, by weight, of polyvinyl alcohol and poly-4-vinylpyridine, at a coverage of about 900 mgs./$ft.^2$ and including about 20 mgs./$ft.^2$ phenyl mercapto tetrazole, to provide a polymeric image-receiving layer.

The two components thus prepared may then be taped together in laminate form, at their respective edges, by means of a pressure-sensitive binding tape extending around, in contact with, and over the edges of the resultant laminate.

A rupturable container comprising an outer layer of lead foil and an inner liner or layer of polyvinyl chloride retaining an aqueous alkaline processing solution comprising:

| | | |
|---|---|---|
| Water | 100 | cc. |
| Potassium hydroxide | 11.2 | gms. |
| Hydroxyethyl cellulose (high viscosity) [commercially available from Hercules Powder Co., Wilmington, Delaware, under the trade name Natrasol 250] | 3.4 | gms. |
| N-phenethyl-α-picolinium bromide | 2.7 | gms. |
| Benzotriazole | 1.15 | gms. |
| Titanium dioxide | 50.0 | gms. |

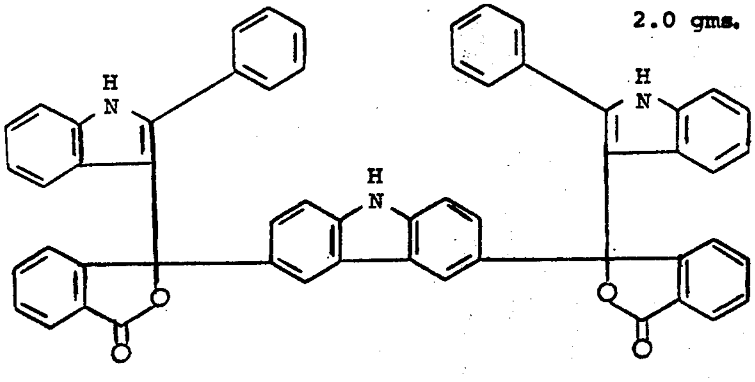

2.0 gms.

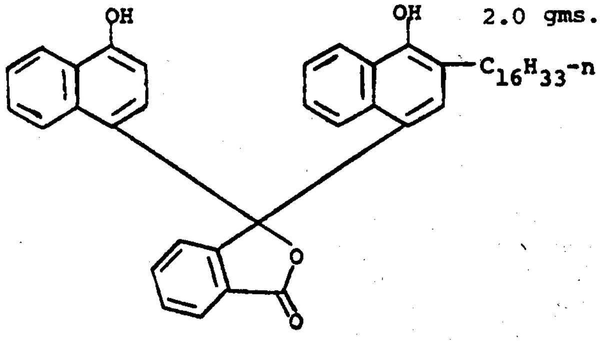

2.0 gms.

may then be fixedly mounted on the leading edge of each of the laminates, by pressure-sensitive tapes interconnecting the respective containers and laminates, such that, upon application of compressive pressure to a container, its contents may be distributed, upon rupture of the container's marginal seal, between the polymeric image-receiving layer and next adjacent gelatin layer.

The photosensitive composite film units may be exposed through step wedges to selectively filter radiation incident on the transparent polyethylene terephthalate layer and processed by passage of the exposed film units through appropriate pressure-applying members, such as suitably gapped, opposed rolls, to effect rupture of the container and distribution of its contents. During processing, the multicolor dye transfer image formation may be viewed through the transparent polyethylene terephthalate layer against the titanium dioxide background provided by distribution of the pigment containing processing composition between the polymeric image-receiving layer and gelatin layer 9 of the photosensitive component. The film unit may be exposed to incident light and the formation of the image may be viewed upon distribution of the processing composition by reason of the protection against incident radiation afforded the photosensitive silver halide emulsion layers by the optical filter agents and by reason of the effective reflective background afforded by the titanium dioxide.

The film unit detailed above is similar to that shown in FIG. 2 and related FIGS. 3 and 4 of aforementioned copending U.S. patent application Ser. No. 101,968. The negative component of the film unit including the photosensitive strata and associated dye-image-forming material; the positive component including the timing, neutralizing and dyeable layers; and the processing composition including its components, such as, the alkaline material and various addenda are described in detail in application Ser. No. 101,968. For convenience, the specification of this application is specifically incorporated herein.

Besides the above photosensitive element, the dyes of the present invention may be employed in composite photosensitive elements, in general, where the dyeable stratum along with any associated layers may be contained together with the photosensitive strata as a unitary film unit which may be termed an integral negative-positive film unit comprising a negative component including the aforementioned essential layers and a positive component including at least the dyeable stratum in which the color transfer image is to be formed. The essential layers are preferably contained on a transparent dimensionally stable layer or support member positioned closest to the dyeable stratum so that the resulting transfer image is viewable through this transparent layer. Most preferably another dimensionally stable layer which may be transparent or opaque is positioned on the opposed surface of the essential layers so that the aforementioned essential layers are sandwiched or confined between a pair of dimensionally stable layers or support members, at least one of which is transparent to permit viewing therethrough of a color transfer image obtained as a function of development of the exposed film unit in accordance with the known color diffusion transfer processes. It will be appreciated that all of these film units, like the specific one detailed above, may optionally contain other layers performing specific desired functions, e.g., spacer layers, pH-reducing layers, etc.

Examples of such integral negative-positive film units for preparing color transfer images viewable without separation are those described and claimed in aforementioned U.S. Pat. No. 3,415,644 and in U.S. Pat. Nos. 3,415,645, 3,415,646, 3,473,925, and 3,573,043.

In general, the film units of the foregoing description, e.g., those described in the aforementioned patents and/or copending applications, are exposed to form a developable image and thereafter developed by applying the appropriate processing composition to develop exposed silver halide and to form, as a function of development, an imagewise destribution of diffusible dye image-providing material which is transferred, at least in part by diffusion, to the dyeable stratum to impart thereto the desired color transfer image, e.g., a positive color transfer image. Common to all of these systems is the provision of a reflecting layer between the dyeable stratum and the photosensitive strata to mask effectively the latter and to provide a background for viewing the color image contained in the dyeable stratum, whereby this image is viewable without separation, from the other layers or elements of the film unit. As discussed previously, in some embodiments this reflecting layer is provided prior to photoexposure, e.g., as a preformed layer included in the essential layers of the laminar structure comprising the film unit, and in others it is provided at some time thereafter, e.g., by including a suitable light-reflecting agent, for example, a white pigment, such as, titanium dioxide, in the processing composition. As an example of such a preformed layer, mention may be made of that disclosed in the copending applications of Edwin H. Land, U.S. Ser. Nos. 846,441, filed July 31, 1969, and 3,645, filed Jan. 19, 1970 and now U.S. Pat. Nos. 3,615,421 and 3,620,724. The reflecting pigment may be generated in situ as is disclosed in the copending applications of Edwin H. Land, U.S. Ser. Nos. 43,741 and 43,742, both filed June 5, 1970 and now U.S. Pat. Nos. 3,647,434 and 3,647,435, respectively. In a particularly preferred form, such film units are employed in conjunction with a rupturable container, such as, that used above, containing the processing composition having the light-reflecting agent incorporated therein which container is adapted upon application of pressure of distributing its contents to develop the exposed film unit and to provide the light-reflecting layer.

As noted previously, the photographic use of the dyes of the present invention as optical filter agents to prevent post-exposure fogging of a selectively exposed photosensitive material is not limited to diffusion transfer processes nor to such processes employing composite photosensitive elements. While the use of such dyes in composite multicolor diffusion transfer film units is a particularly preferred embodiment of the present invention, these dyes may be used with equally effective results in any photographic process where it is desired to protect a photosensitive material from incident radiation actinic to the photosensitive material within the wavelength range capable of being absorbed by the dye. For example, the subject dyes may be used in conventional tray photographic processing as a component of the processing bath, or they may be present in a layer coextensive with one or both surfaces of a layer of photosensitive material to be processed using conventional tray procedures, provided that they are non-light-absorbing prior to photoexposure and also subsequent to developing the latent image unless the layer containing the dye is to be removed subsequent to processing. In such procedures, the photo-exposed photosensitive material will, of course, be transferred from the camera to the processing bath in the absence of radiation actinic to the material.

The subject dyes also may be employed in diffusion transfer processes where the photosensitive and image-receiving elements are separated subsequent to the formation of a transfer image or where a spreader sheet is separated from the photosensitive element to reveal a final image in the negative. In addition to the composite diffusion transfer structures described above, the subject dyes may be used with composite diffusion transfer film units where the final image is to be viewed by transmitted light. Also they may be used in composite film units specifically adapted, for example, for forming a silver transfer image, for developing a negative silver image by monobath processing, for obtaining an additive color image, and for obtaining a dye image by the silver dye bleach process which structures are described in detail in aforementioned copending U.S. application Ser. No. 101,968 particularly with reference to FIGS. 10 to 13 of the application's drawings.

Although the invention has been discussed in detail throughout employing dye developers, the preferred image-providing materials, it will be readily recognized that other, less preferred, image-providing materials may be substituted in replacement of the preferred dye developers in the practice of the invention. For example, there may be employed dye image-forming materials such as those disclosed in U.S. Pat. Nos. 2,647,049; 2,661,293; 2,698,244; 2,698,798; 2,802,735; 3,148,062; 3,227,550; 3,227,551; 3,227,552; 3,227,554; 3,243,294; 3,330,655; 3,347,671; 3,352,672; 3,364,022; 3,443,939; 3,443,940; 3,443,941; 3,443,943; etc., wherein color diffusion transfer processes are described which employ color coupling techniques comprising, at least in part, reacting one or more color developing agents and one or more color formers or couplers to provide a dye transfer image to a superposed image-receiving layer and those disclosed in U.S. Pat. No. 2,774,668 and 3,087,817, wherein color diffusion transfer processes are described which employ the imagewise differential transfer of complete dyes by the mechanisms therein described to provide a transfer dye image to a contiguous image-receiving layer, and thus including the employment of image-providing materials in whole or in part initially insoluble or nondiffusible as disposed in the film unit which diffuse during processing as a direct or indirect function of exposure.

In view of the foregoing, it will be readily apparent that the subject dyes are useful generally in photographic processes for producing silver, monochromatic and multi-color images using any photosensitive material including conventional and direct positive silver halide emulsions. Depending upon the selected photosensitive material, one or more of the dyes may be used alone or in combination with another optical filter agent, such as another light-absorbing dye, which second dye may be non-color-changing or another pH sensitive dye. If the selected dye or dyes do not possess the desired stability in the processing composition for long term storage therein, they may be initially disposed in the film structure or stored in a double-compartmented pod or in one of two associated pods separate from the processing solution until such time as the pod(s) are ruptured whereupon the dyes are admixed with the processing solution.

Since certain changes may be made in the above product and process without departing from the scope of the invention herein involved, it is intended that all matter contained in the above description or shown in the accompanying drawings shall be interpreted as illustrative and not in a limiting sense.

What is claimed is:

1. An indicator dye of the formula:

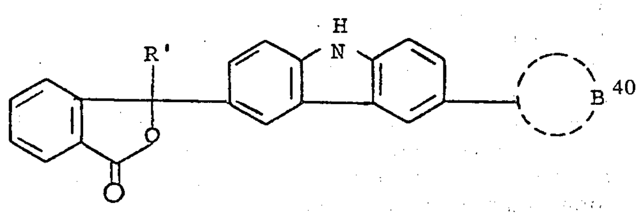

wherein B represents

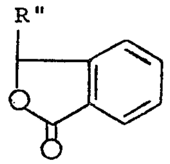

or

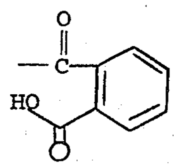

wherein R' and R'' the same are selected from

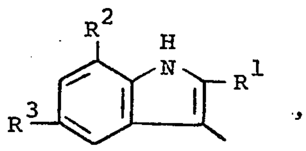

,

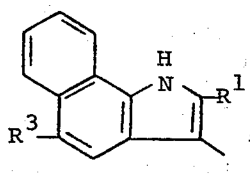

,

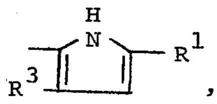

,

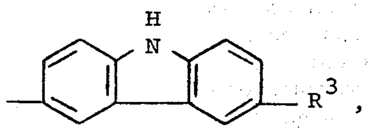

,

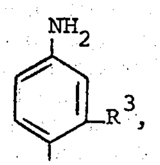

,

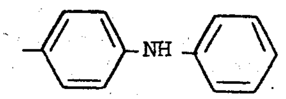

,

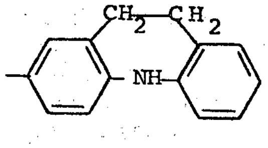

,

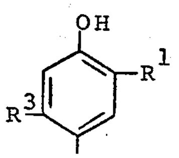

,

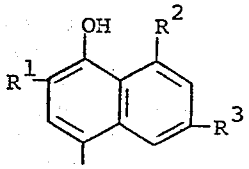

wherein $R^1$ is selected from hydrogen, alkyl having 1 to 20 carbon atoms, phenyl and a hydrogen-bonding group forming a 5-, 6- or 7-membered intramolecular hydrogen-bonded ring with the adjacent -NH- or -OH and selected from carboxy, hydroxy, o-hydroxyphenyl, bis trifluoromethyl carbinol, sulfonamido and sulfamoyl, $R^2$ is selected from hydrogen and a hydrogen-bonding group forming a 5-, 6- or 7-membered intramolecular hydrogen-bonded ring with the adjacent -NH or -OH and selected from carboxy, hydroxy, o-hydroxyphenyl, bis trifluoromethyl carbinol, sulfonamido and sulfamoyl, not more than one of $R^1$ and $R^2$ being a hydrogen-bonding group, and $R^3$ is selected from hydrogen, phenyl, alkyl having 1 to 20 carbon atoms and alkoxy having 1 to 20 carbon atoms.

2. A dye as defined in claim 1 wherein B represents

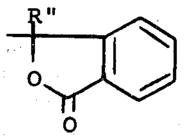

3. A dye as defined in claim 2 wherein said R' and R'' are

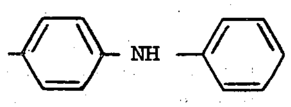

4. A dye as defined in claim 2 wherein said R' and R'' are

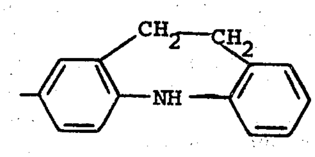

5. A dye as defined in claim 2 wherein said R' and R'' are

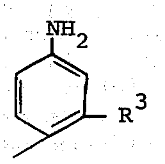

6. A dye as defined in claim 2 wherein R' and R'' are

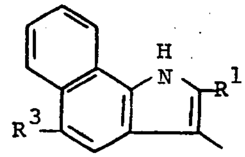

7. A dye as defined in claim 6 wherein R¹ is a hyrogen-bonding group.

8. A dye as defined in claim 7 wherein R¹ is carboxy.

9. A dye as defined in claim 2 wherein R' and R'' are

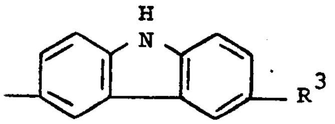

10. A dye as defined in claim 2 wherein R' are R'' are

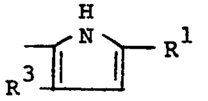

11. A dye as defined in claim 10 wherein R¹ is a hydrogen-bonding group.

12. A dye as defined in claim 11 wherein R¹ is o-hydroxyphenyl.

13. A dye as defined in claim 2 wherein R' and R'' are

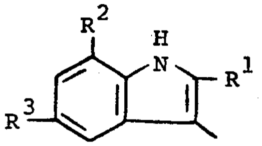

14. A dye as defined in claim 13 wherein R¹ is a hydrogen-bonding group.

15. A dye as defined in claim 14 wherein R¹ is o-hydroxyphenyl.

16. A dye as defined in claim 2 wherein R' and R'' are

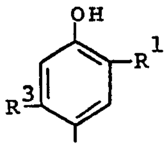

17. A dye as defined in claim 2 wherein R' and R'' are

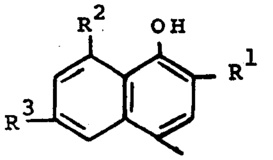

18. A dye as defined in claim 1 wherein B represents

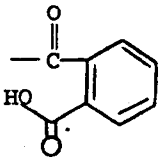

19. A dye as defined in claim 18 wherein R' is

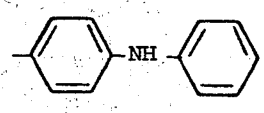

20. A dye as defined in claim 18 wherein R' is

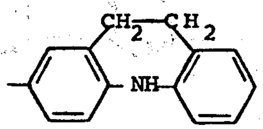

21. A dye as defined in claim 18 wherein R' is

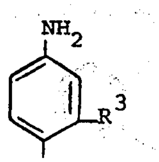

22. A dye as defined in claim 18 wherein R' is

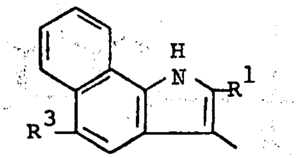

23. A dye as defined in claim 18 wherein R' is

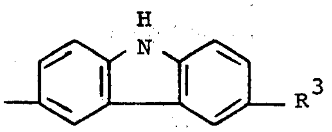

24. A dye as defined in claim 18 wherein R' is

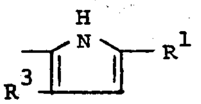

25. A dye as defined in claim 18 wherein R' is

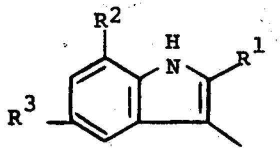

26. A dye as defined in claim 18 wherein R' is

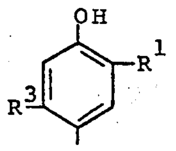

27. A dye as defined in claim 18 wherein R' is

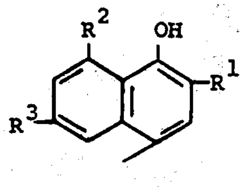

28. The compound of the formula
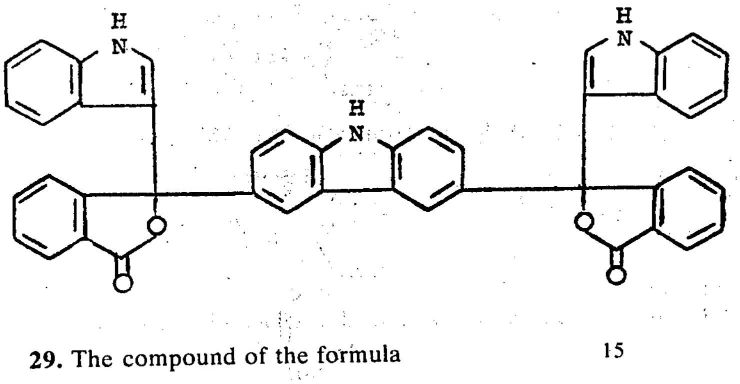
29. The compound of the formula
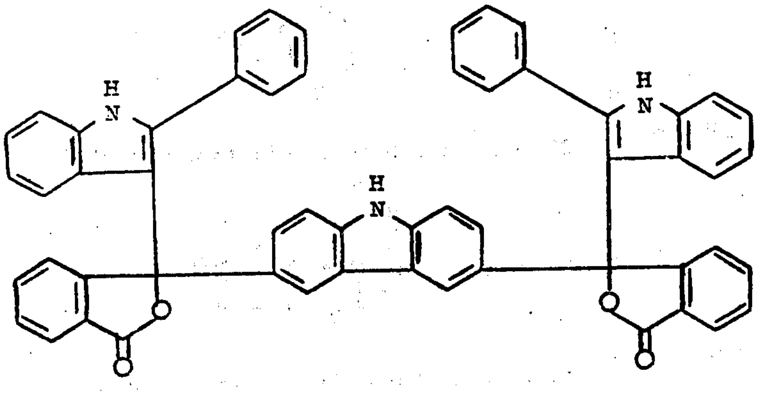
30. The compound of the formula
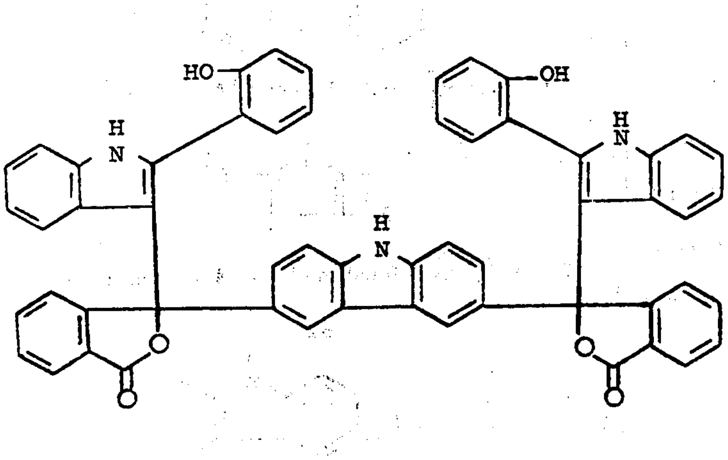
31. The compound of the formula
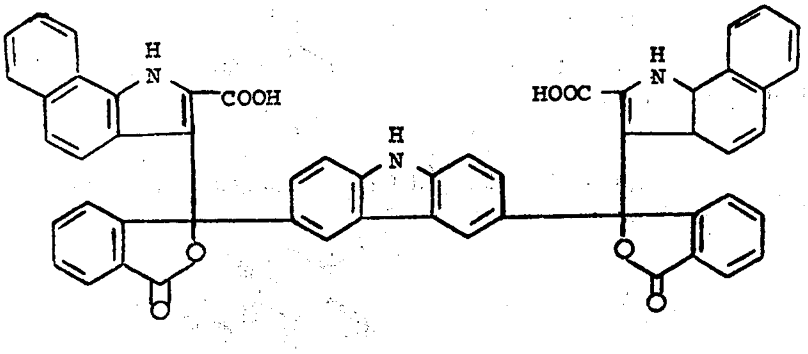

32. The compound of the formula
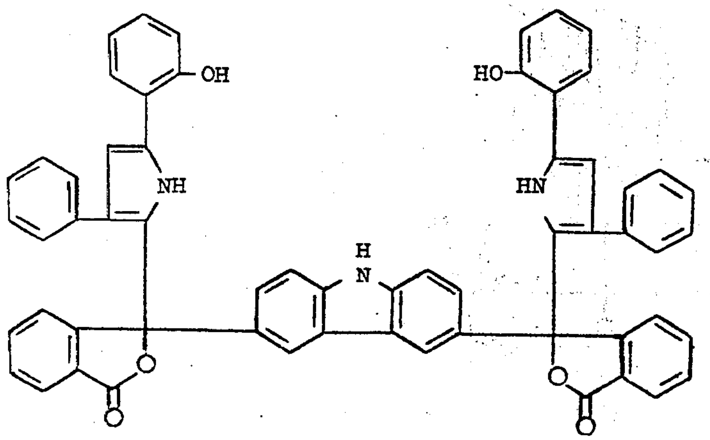
33. The compound of the formula
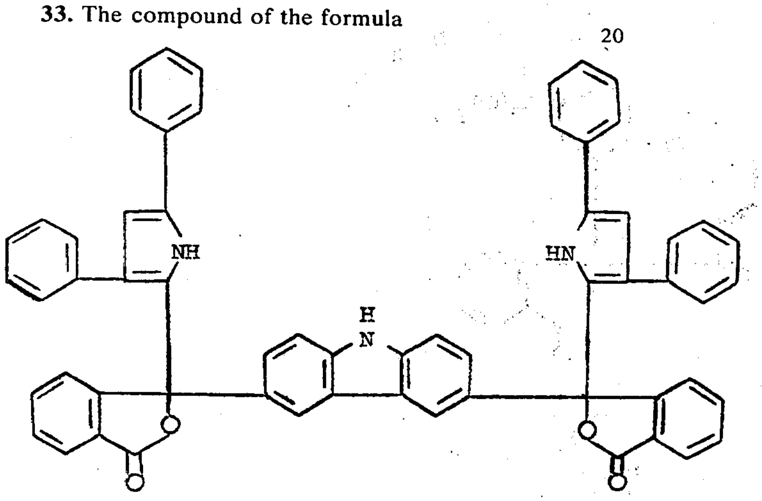
34. The compound of the formula
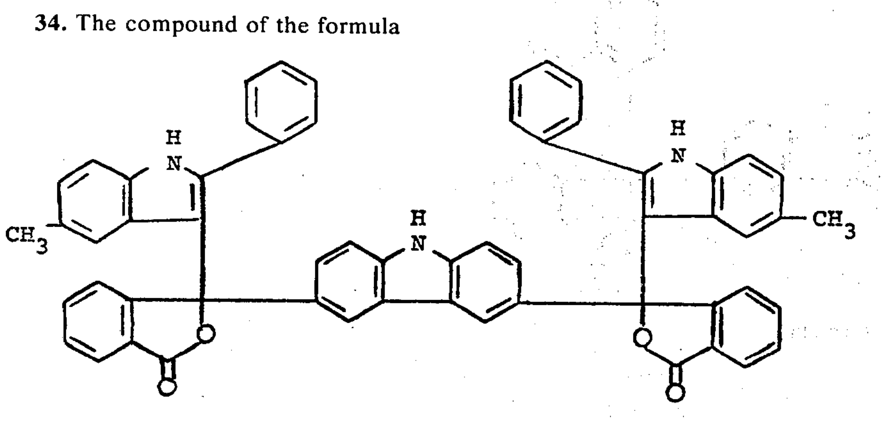
35. The compound of the formula
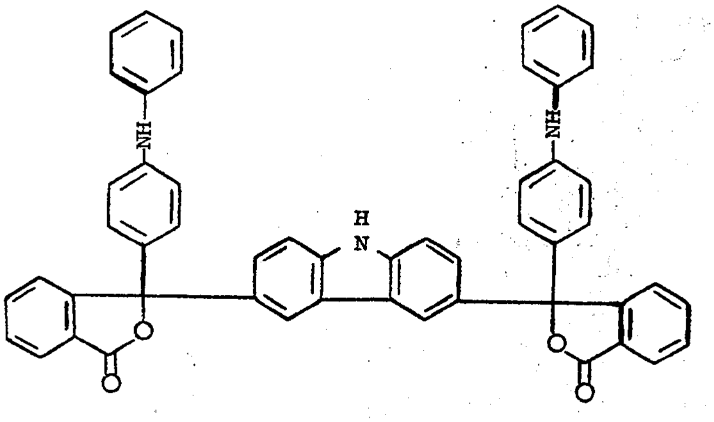

36. The compound of the formula
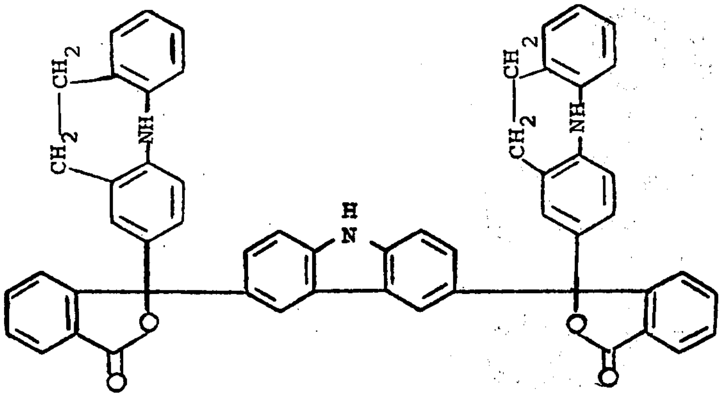
37. The compound of the formula
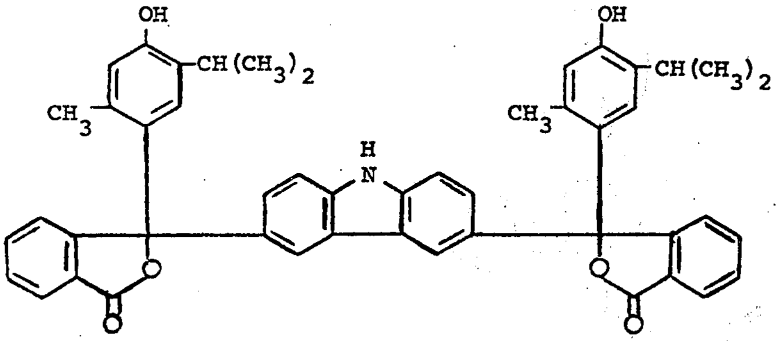
38. The compound of the formula
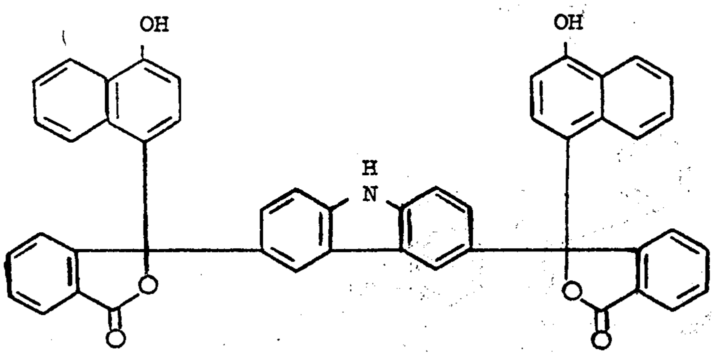
39. The compound of the formula
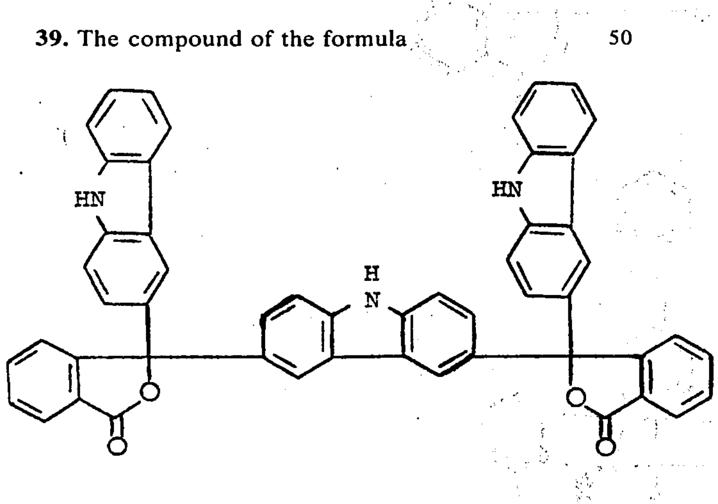

40. The compound of the formula
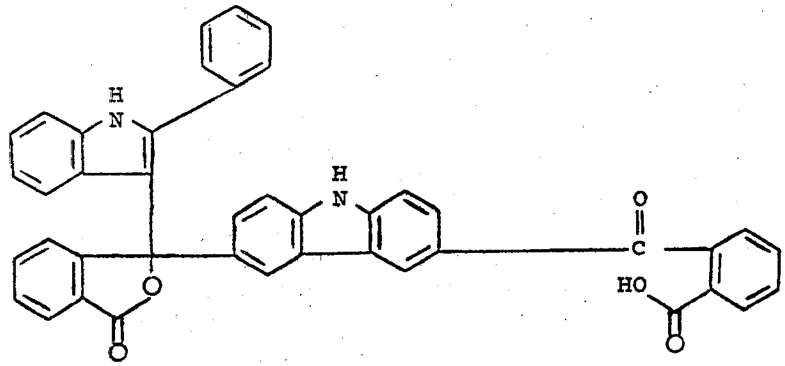
41. The compound of the formula
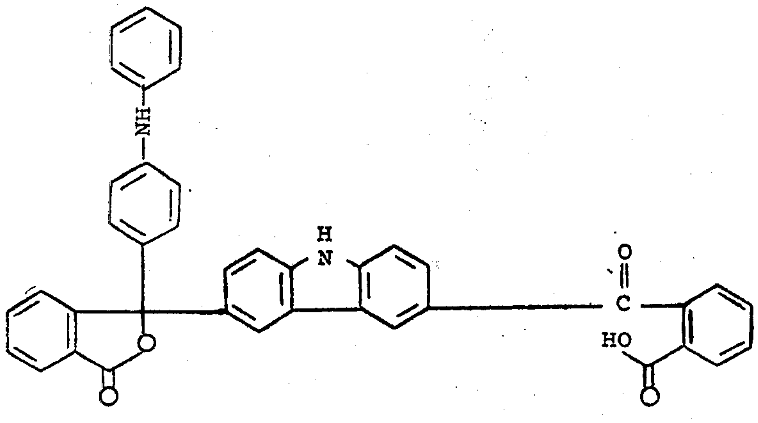
42. The compound of the formula
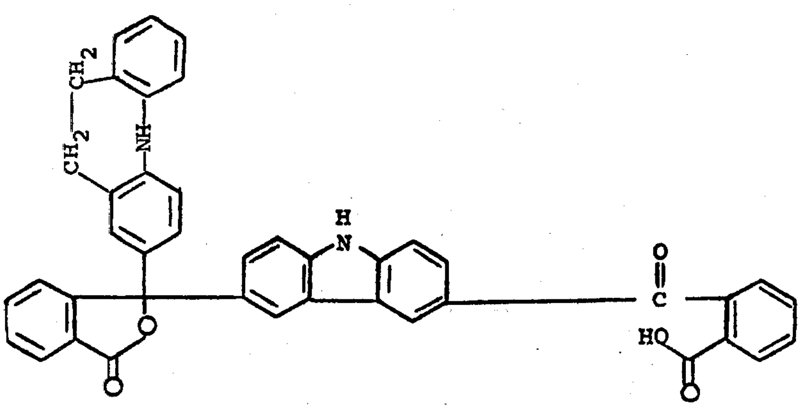
43. A method of preparing an indicator dye which comprises reacting 2 equivalents of (a) an aromatic compound selected from an N-heterocyclic aryl compound having the formula
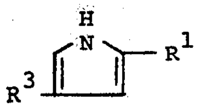
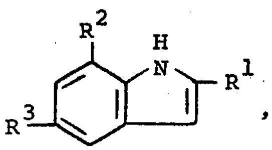
,
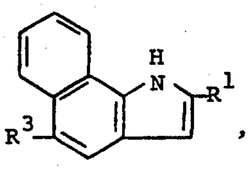
,
or
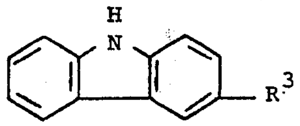

and a carbocyclic aryl compound having the formula

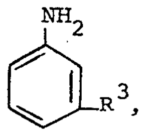,
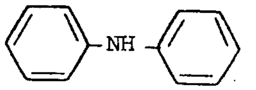,
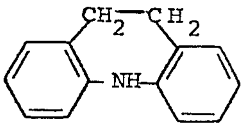,
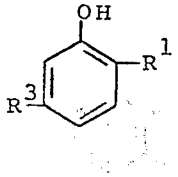

or

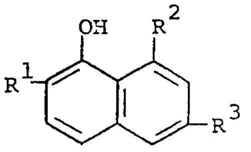

wherein $R^1$ is selected from hydrogen, alkyl having 1 to 20 carbon atoms, phenyl and a hydrogen-bonding group forming a 5-, 6- or 7-membered intramolecular hydrogen-bonded ring with the adjacent -NH- or -OH and selected from carboxy, hydroxy, o-hydroxyphenyl, bis trifluoromethyl carbinol, sulfonamido and sulfamoyl, $R^2$ is selected from hydrogen and a hydrogen-bonding group forming a 5-, 6- or 7-membered intramolecular hydrogen-bonded ring with the adjacent —NH— or —OH and selected from carboxy, hydroxy, o-hydroxyphenyl, bis trifluoromethyl carbinol, sulfonamido and sulfamoyl, not more than one of $R^1$ and $R^2$ being a hydrogen-bonding group, and $R^3$ is selected from hydrogen, phenyl, alkyl having 1 to 20 carbon atoms, and alkoxy having 1 to 20 carbon atoms and (b) 1 equivalent of a 3,6-bis-(o-carboxybenzoyl)carbazole in the presence of a condensing agent selected from acetic anhydride, p-toluenesulfonic acid, zinc chloride and boron trifluoride-etherate to form the corresponding 3,6-bis-($C_6H_4·CO·O·CR$-) carbazole wherein R is an aryl radical selected from

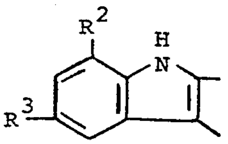,
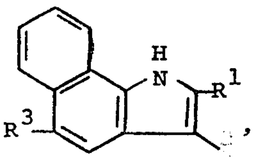,
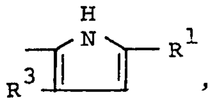,
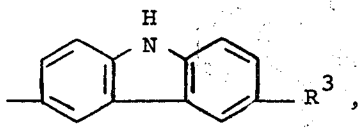,
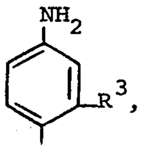,
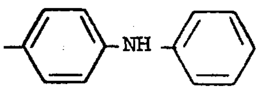,
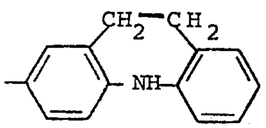,
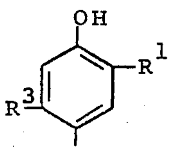

and

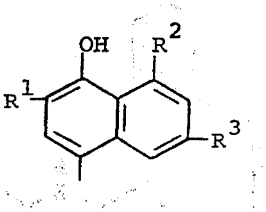

wherein $R^1$, $R^2$ and $R^3$ have the same meaning given above and heating said last-named compound at reflux in an aqueous alkanol solution of alkaline hydroxide to form the corresponding 3-($C_6H_4·CO·O·CR$-)-6-(carboxybenzoyl) carbazole wherein R has the same meaning given above.

44. A method as defined in claim 43 wherein said alkaline hydroxide in sodium hydroxide.

45. A method as defined in claim 43 wherein said aromatic compound is an N-heterocyclic aryl compound.

46. A method as defined in claim 45 wherein said comdensing agent is acetic anhydride.

47. A method as defined in claim 46 wherein said N-heterocyclic aryl compound is

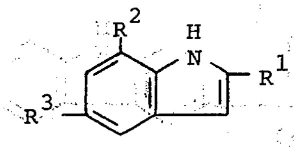

48. A method as defined in claim 43 wherein said aromatic compound is a carbocyclic aryl compound.

49. A method as defined in claim 48 wherein said condensing agent is boron trifluoride-etherate.

50. A method as defined in claim 49 wherein said carbocyclic aryl compound is

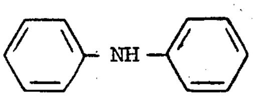

51. A method as defined in claim 49 wherein said carbocyclic aryl compound is

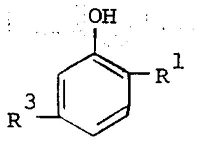

52. A method as defined in claim 49 wherein said carbocyclic aryl compound is

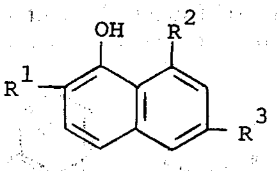

* * * * *